(12) United States Patent
Bouaziz et al.

(10) Patent No.: US 9,056,888 B2
(45) Date of Patent: Jun. 16, 2015

(54) DERIVATIVES OF 3-O-(3',3'-DIMETHYLSUCCINYL)-BETULINIC ACID

(75) Inventors: Serge Bouaziz, Montreuil (FR); Pascale Coric, Paris (FR); Pierre Boulanger, Lyons (FR); Saw-See Hong, Lyons (FR); Serge Turcaud, Sartrouville (FR); Florence Souquet, Jossigny (FR); Nathalie Chazal, Marguerittes (FR); Laurence Briant, Gallargues-le-Monteux (FR)

(73) Assignees: Centre National de la Recherche Scientifique (FR); Universite Paris Descartes (FR)

( * ) Notice: Subject to any disclaimer, the term of this patent is extended or adjusted under 35 U.S.C. 154(b) by 79 days.

(21) Appl. No.: 13/608,486

(22) Filed: Sep. 10, 2012

(65) Prior Publication Data
US 2013/0096094 A1    Apr. 18, 2013

(30) Foreign Application Priority Data
Sep. 12, 2011    (EP) .................................... 11306138

(51) Int. Cl.
*A61K 31/56* (2006.01)
*C07J 53/00* (2006.01)
*C07J 63/00* (2006.01)

(52) U.S. Cl.
CPC .............. *C07J 53/002* (2013.01); *C07J 63/008* (2013.01)

(58) Field of Classification Search
CPC .............................. C07J 53/002; C07J 63/008
USPC ............................ 514/169, 182; 552/502, 510
See application file for complete search history.

(56) References Cited

U.S. PATENT DOCUMENTS

| | | | |
|---|---|---|---|
| 7,026,305 B2* | 4/2006 | Chen et al. .................... | 514/169 |
| 7,381,717 B2* | 6/2008 | Chen et al. .................... | 514/169 |
| 2006/0205697 A1* | 9/2006 | Robinson et al. ............. | 514/129 |
| 2007/0203103 A1* | 8/2007 | Hemp et al. ................... | 514/169 |
| 2008/0207573 A1* | 8/2008 | Yager et al. ................... | 514/171 |
| 2009/0105203 A1* | 4/2009 | Yager et al. ................... | 514/182 |
| 2011/0144069 A1* | 6/2011 | Yager et al. ................... | 514/171 |
| 2011/0152229 A1* | 6/2011 | Chen et al. .................... | 514/182 |

OTHER PUBLICATIONS

Aiken, et al., "Betulinic Acid Derivatives as HIV-1 Antivirals", Trends Mol Med, 2005, pp. 31-36.
Carriere, et al., "Sequence Requirements for Encapsidation of Deletion Mutants and Chimeras of Human Immunodeficiency Virus Type 1 Gag Precursor into Retrovirus-Like Particles", J Virol, 1995, pp. 2366-2377.
Chazal, et al., "Phenotypic Characterization of Insertion Mutants of the Human Immunodeficiency Virus Type 1 Gag Precursor Expressed in Recombinant Baculovirus-Infected Cells", J Virol, 1994, pp. 111-122.
Coric, et al., "Synthesis and Biological Evaluation of a New Derivative of Bevirimat that Targets the Gag CA-SP1 Cleavage Site", European Journal of Medicinal Chemistry, 2012, (Entirety of Manuscript).
DaFonseca, et al., "The 3-0-(3',3'-Dimethylsuccinyl) Derivative of Betulinic Acid (DSB) Inhibits the Assembly of Virus-Like Particles in HIV-1 Gag Precursor-Expressing Cells", Antiviral Ther, 2007, pp. 1185-1203.
Mosmann, Tim, "Rapid Colorimetric Assay for Cellular Growth and Survival: Application to Proliferation and Cytotoxicity Assays", J Immunol Methods, 1983, pp. 55-63.
Muller, et al., "Human Immunodeficiency Virus Type 1 Vpr Protein Is Incorporated into the Virion in Significantly Smaller Amounts than Gag and Is Phosphorylated in Infected Cells", J Virol, 2000, pp. 9727-9731.
Muriaux, et al., "RNA is a Structural Element in Retrovirus Particles", Proc Natl Acad Sci USA, 2001, pp. 5246-5251.
Nguyen, et al., "The Prototype HIV-1 Maturation Inhibitor, Bevirimat, Binds to the CA-SP1 Cleavage Site in Immature Gag Particles", Retrovirology, 2011, pp. 1-13.
Selig, et al., "Interaction with the p6 Domain of the Gag Precursor Mediates Incorporation into Virions of Vpr and Vpx Proteins from Primate *Lentiviruses*", J Virol, 1999, pp. 592-600.
Wilk, et al., "Organization of Immature Human Immunodeficiency Virus Type 1", J Virol, 2001, pp. 759-771.
Wuts, Peter G.M., "Protective Groups in Organic Synthesis", 2007, pp. 237-241.
Yao, et al., "Analysis of HIV-1 Vpr Determinants Responsible for Cell Growth Arrest in *Saccharomyces cerevisiae*", Retrovirology, 2004.

* cited by examiner

*Primary Examiner* — My-Chau T Tran
(74) *Attorney, Agent, or Firm* — Banner & Witcoff, Ltd.

(57) ABSTRACT

The present invention relates to compounds of the following formula (I):

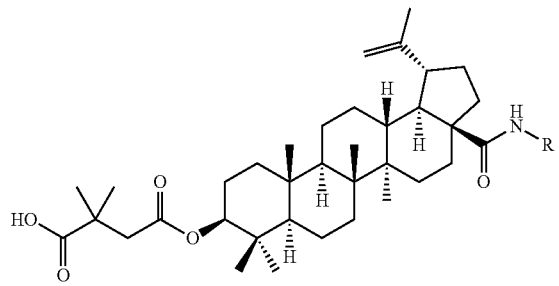

Figure 1:
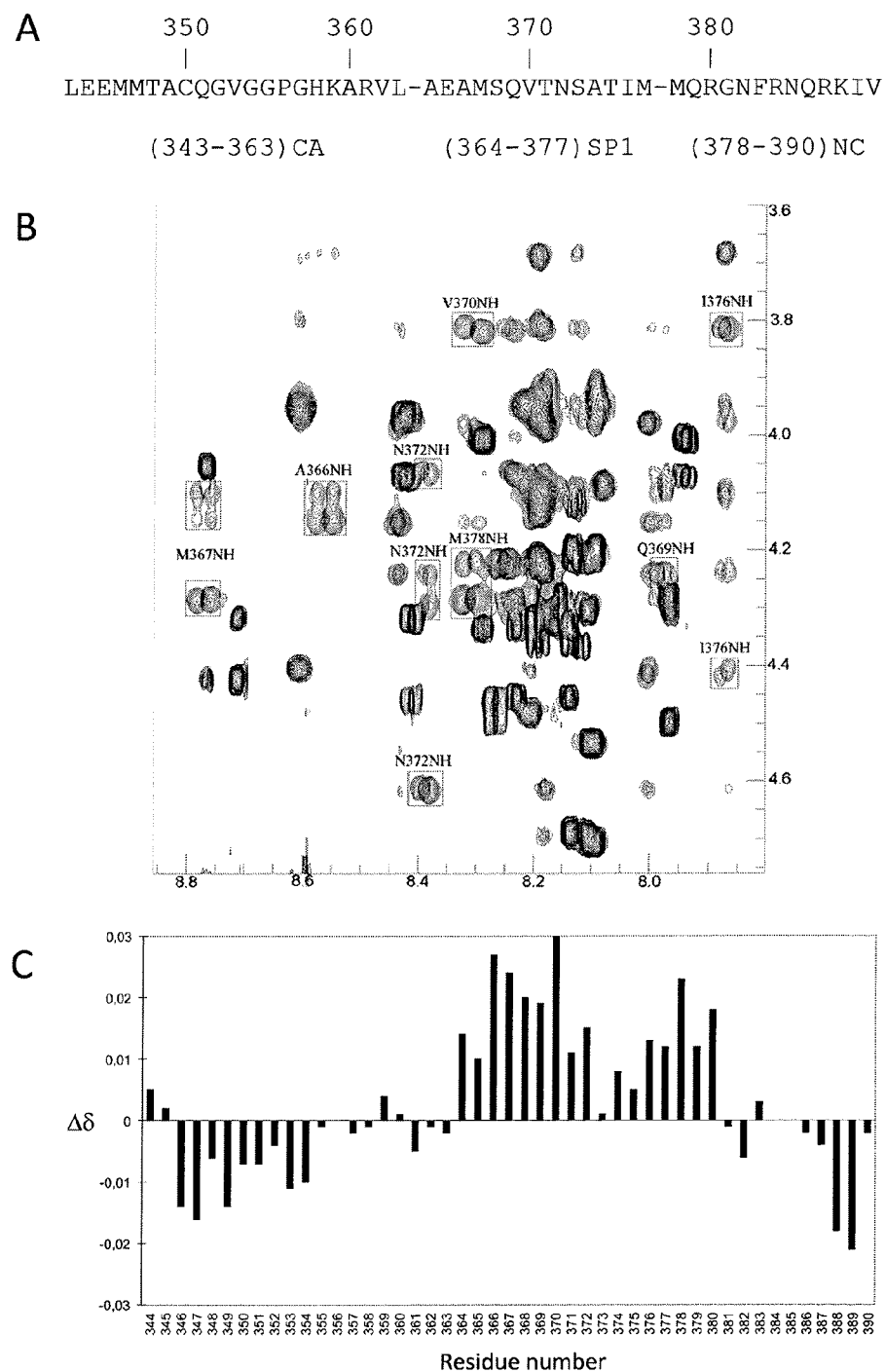

or a pharmaceutically acceptable salt thereof, a stereoisomer or a mixture of stereoisomers in any proportion, in particular a mixture of enantiomers, and particularly a racemate mixture,
in which R represents a $(C_1-C_{10})$alkyl group substituted with one or more, preferably one or two, groups chosen from COOH and $NHR^1$,
with $R^1$ representing a hydrogen atom or a -Alk, —C(O)-Alk or —C(O)O-Alk group, Alk representing a $(C_1-C_6)$alkyl group,
as well as a method for preparing them, and their use as a medicine, notably for treating an infection with a retrovirus such as HIV.

21 Claims, 4 Drawing Sheets

SEQUENCE LISTING

```
<160> NUMBER OF SEQ ID NOS: 3

<210> SEQ ID NO 1
<211> LENGTH: 48
<212> TYPE: PRT
<213> ORGANISM: Human immunodeficiency virus

<400> SEQUENCE: 1

Leu Glu Glu Met Met Thr Ala Cys Gln Gly Val Gly Gly Pro Gly His
1               5                   10                  15

Lys Ala Arg Val Leu Ala Glu Ala Met Ser Gln Val Thr Asn Ser Ala
            20                  25                  30

Thr Ile Met Met Gln Arg Gly Asn Phe Arg Asn Gln Arg Lys Ile Val
        35                  40                  45

<210> SEQ ID NO 2
<211> LENGTH: 6
<212> TYPE: PRT
<213> ORGANISM: Artificial
<220> FEATURE:
<223> OTHER INFORMATION: polypeptide tag

<400> SEQUENCE: 2

His His His His His His
1               5

<210> SEQ ID NO 3
<211> LENGTH: 4
<212> TYPE: PRT
<213> ORGANISM: Artificial
<220> FEATURE:
<223> OTHER INFORMATION: polypeptide linker

<400> SEQUENCE: 3

Gly Ser Gly Ser
1
```

DERIVATIVES OF 3-O-(3',3'-DIMETHYLSUCCINYL)-BETULINIC ACID

The present invention relates to derivatives of 3-O-(3',3'-dimethylsuccinyl)-betulinic acid, a method for preparing them and their use in the treatment of an infection with a retrovirus such as HIV.

Most of the anti-HIV-1 drug inhibitors target the enzymatic activities catalyzed by the reverse transcriptase (RT), the integrase (IN) or the protease (PR) and have caused the emergence of multidrug-resistant HIV-1 strains. Thus, the scientific community has been involved in the discovery of new targets to fight AIDS and in the development of new molecules directed against these targets. The assembly of the HIV-1 Gag precursor (Pr55Gag) and the maturation steps of the virus replication represent attractive targets for the design of new molecules able to inhibit the retroviral replication.

The polyprotein Gag is necessary and sufficient for assembly of virus-like pseudoparticles (VLP). During or subsequently to assembly of the entire HIV-1 particle, Gag is cleaved by the PR in four mature proteins: matrix (MA), capsid (CA), nucleocapsid (NC) and p6. Two extra spacer peptides, SP1 and SP2, separating CA/NC and NC/p6 respectively, are released. This maturation process is timely regulated: the first cleavage occurs between SP1 and NCp7 leading to the intermediate MA-CA-SP1, which is then cleaved to MA and precursor CA-SP1 (p25). The cleavage of p25 occurs late in the virus life cycle and generates the mature CA (p24) and the peptide SP1. This is a crucial step for the proper formation of mature and infectious viral particles.

Recently, it has been demonstrated that the inhibition at the CA-SP1 cleavage site causes the production of defective and non-infectious viral particles. Moreover, the region surrounding the CA-SP1 domain plays an important role in the morphogenesis of the virion. Mutations of residues at the CA-SP1 junction or within the peptide SP1, showing a high degree of conservation within their four N-terminal residues, have been performed in different HIV-1 isolates and other primate lentiviruses. It has been suggested that these mutations block the processing step and result in the production of virions with aberrant cores. The peptide SP1 plays a crucial role in the assembly and the maturation steps of HIV-1 replication since it has been shown that the incorporation of the domain SP1 at the C-terminus of CA allows Gag to multimerize.

The accumulation of immature, non-infectious virus particles due to unprocessed or partially processed polyprotein precursors can be provoked by a novel class of antivirals derived from betulinic acid. An important member of this family of antiviral drugs is the 3-O-(3',3'-dimethylsuccinyl)-betulinic acid, abbreviated DSB, known as YK-FH312 or PA-457, and used in the clinics as Bevirimat™. It is synthesized from betulinic acid (BA) which is extracted from the leaves of *Syzigium claviforum*. In the nanomolar range, DSB interferes with the PR-mediated proteolytic cleavage of the Pr55Gag polyprotein substrate at the junction of the capsid (CA) and nucleocapsid (NC) domains, resulting in particles with higher CAp25 content (CAp25=CAp24+SP1) and lower infectivity. In the micromolar range and in a heterologous system, DSB has a negative effect on the assembly and egress of virus-like particles (VLP) formed of Pr55Gag.

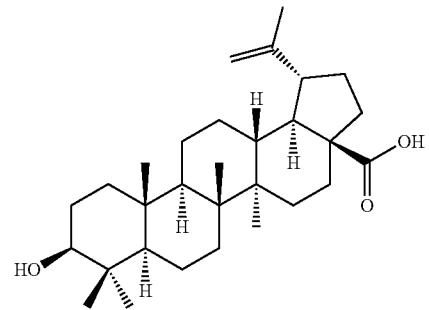

Betulinic acid

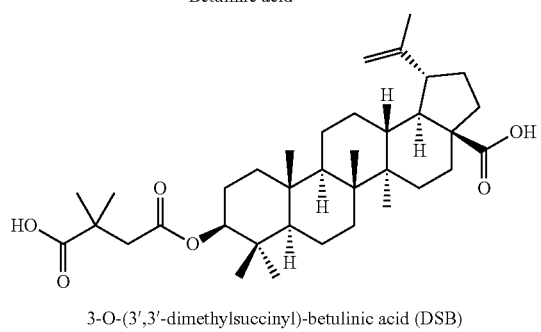

3-O-(3',3'-dimethylsuccinyl)-betulinic acid (DSB)

DSB, the first-in-class HIV maturation inhibitor, shows however a low efficacy because of the natural polymorphism of its target, the CA-SP1 junction in the polyprotein Gag and of low bioavailability.

The inventors of the present invention have discovered that it is possible to obtain anti-HIV agents, with higher solubility and efficacy on maturation inhibition, as well as on assembly inhibition, by substitution of the C-28 position of DSB with particular chains.

These triterpene derivatives were evaluated for their capacity to inhibit HIV-1 replication by blocking the protease (PR)-mediated cleavage at the CA-SP1 junction.

The production of virus from HIV-1 wild-type transfected 293T cells in presence of these compounds was also evaluated and revealed their function as maturation inhibitor.

In parallel, the inventors applied a luciferase-based quantification of VLP production by insect cells to these new derivatives and showed their viral assembly inhibition.

Results show that at the nanomolar range the new compounds and in particular compound 16 are inhibitors of the maturation and that at higher doses (micromolar), they inhibit the particle assembly. This dual property is new and essential, in close relation with the nature of the substituents at the C28 position.

It has been further evidenced that these triterpene derivatives, in particular compound 16, directly bind their target within the P55Gag polyprotein. The interaction of compound 16 with the wild type CA-SP1-NC domain, the amino acid sequence of which is shown in FIG. 1A, was studied by NMR. A NOESY experiment was performed in the presence or absence of compound 16 (FIG. 1B) and the perturbations of the amide proton chemical shifts of the junction were analyzed. Amino acids of the spacer peptide SP1 (A366, M367, V370, N372 and I376) as well as the first residue of NC (M378) are the most perturbed by the presence of compound 16. The variations of the chemical shift [Δδ=δ(without 16)−δ(with 16)] are represented in FIG. 1C. The obtained data confirm the results obtained recently with photoaffinity analogs of Bevirimat™ that were found to crosslink to sequences overlapping the CA-SP1 junction and consistent with previous biochemical data on the effect of Beviramat™ on Gag processing (A. T. Nguyen, C. L. Feasley, K. W. Jackson, T. J. Nitz, K. Salzwedel, G. M. Air, M. Sakalian, The prototype HIV-1 maturation inhibitor, beviramat, binds to the CA-SP1 cleavage site in immature Gag particles, Retrovirology, 8 (2011) 101).

The present invention relates thus to compounds of the following formula (I):

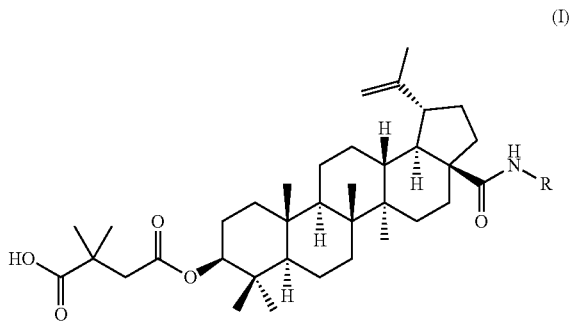

or a pharmaceutically acceptable salt thereof, a stereoisomer or a mixture of stereoisomers in any proportion, in particular a mixture of enantiomers, and particularly a racemate mixture,
in which R represents a $(C_1-C_{10})$alkyl group substituted with one or more, preferably one or two, groups chosen from COOH and $NHR^1$,
with $R^1$ representing a hydrogen atom or a -Alk, —C(O)-Alk or —C(O)O-Alk group, Alk representing a $(C_1-C_6)$alkyl group.

For the purpose of this invention, the term "pharmaceutically acceptable" is intended to mean what is useful to the preparation of a pharmaceutical composition, and what is generally safe and non toxic, for a pharmaceutical use.

The term <<pharmaceutically acceptable salt>> is intended to mean, in the framework of the present invention, a salt of a compound which is pharmaceutically acceptable, as defined above, and which possesses the pharmacological activity of the corresponding compound. Such salts comprise:
(1) hydrates and solvates,
(2) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and
(3) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Within the meaning of this invention, "steroisomers" is intended to designate diastereoisomers and enantiomers. These are therefore optical isomers. Stereoisomers which are not mirror images of one another are thus designated as "diastereoisomers", and stereoisomers which are non-superimposable mirror images are designated as "enantiomers".

A carbon atom bond to four non-identical substituents is called a "chiral centre".

An equimolar mixture of two enantiomers is called a racemate mixture.

The term "$(C_1-C_{10})$alkyl", as used in the present invention, refers to a straight or branched saturated hydrocarbon chain containing from 1 to 10 carbon atoms.

The term "$(C_1-C_6)$alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

Advantageously, R represents a $(C_1-C_6)$alkyl group substituted with one or more, preferably one or two, groups chosen from COOH and $NHR^1$.

R can represent in particular a group —$(CHR^2)$—$(CHR^3)_n$—X, in which:
n represents 0 or 1,
X represent a group COOH or $NHR^1$, and
$R^2$ and $R^3$ represent, independently of each other, a hydrogen atom or a $(C_1-C_8)$alkyl group, preferably a $(C_1-C_4)$ alkyl group, optionally substituted with a COOH or $NHR^1$ group.

Preferably, at least $R^2$ or $R^3$ represents a hydrogen atom.
In the definition of R above, $R^1$ can represent advantageously a hydrogen atom or a —C(O)O-Alk group, in particular $R^1$ can represent H or a Boc group (tert-butyloxycarbonyl).

In particular, R will be chosen from the following groups:

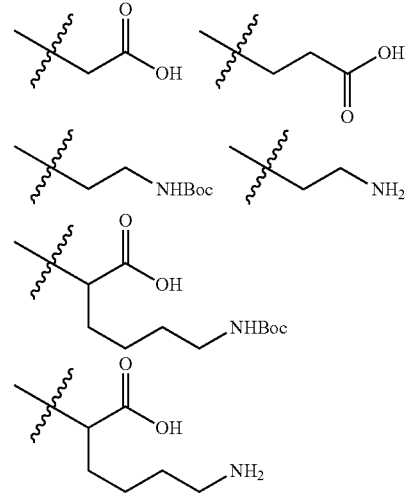

The compound of formula (I) will be preferably chosen from the following compounds:

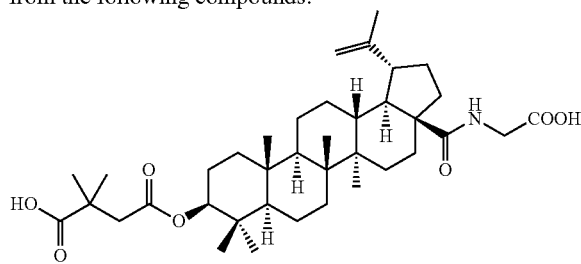

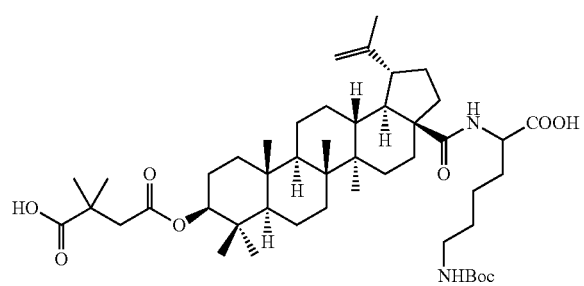

15

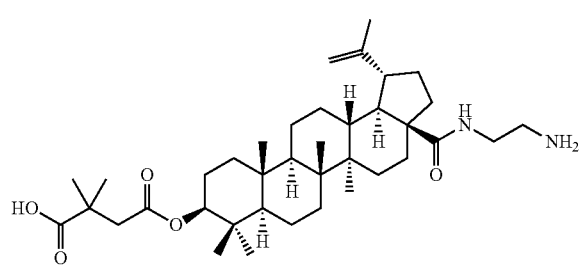

16

Preferably, the compound of the present invention will be compound 16.

The present invention relates also to the above mentioned compounds of formula (I) as a medicine.

These compounds can be useful for the treatment of an infection with a retrovirus such as HIV, and in particular HIV-1.

The invention concerns also the use of a compound of formula (I) for the preparation of a medicament intended to be used in the treatment of an infection with a retrovirus such as HIV, and in particular HIV-1.

The invention concerns also a method for treating an infection with a retrovirus such as HIV, and in particular HIV-1, comprising the administration to a person in need thereof of an efficient amount of at least one compound of formula (I).

The present invention relates also to a pharmaceutical composition comprising at least one compound of formula (I) and at least one pharmaceutically acceptable vehicle.

The pharmaceutical compositions of the invention can be intended to oral, sublingual, subcutaneous, intramuscular, intravenous, transdermal, local or rectal administration. The active ingredient can be administered in unit forms for administration, mixed with conventional pharmaceutical carriers, to animals or to humans. Suitable unit forms for administration comprise the forms for oral administration, such as tablets, gelatin capsules, powders, granules and oral solutions or suspensions, the forms for sublingual and buccal administration, the forms for subcutaneous, intramuscular, intravenous, intranasal or intraoccular administration and the forms for rectal administration.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

A preparation in the form of a syrup or an elixir may contain the active ingredient together with a sweetener, an antiseptic, or also a taste enhancer or a suitable coloring agent.

The water-dispersible powders or granules may contain the active ingredient mixed with dispersing agents or wetting agents, or suspending agents, and with flavor correctors or sweeteners.

For rectal administration, suppositories are used which are prepared with binders which melt at rectal temperature, for example cocoa butter or polyethylene glycols.

For parenteral, intranasal or intraoccular administration, aqueous suspensions, isotonic saline solutions or sterile and injectable solutions which contain pharmacologically compatible dispersing agents and/or wetting agents are used.

The active principle may also be formulated in the form of microcapsules, optionally with one or more carrier additives.

The compounds of the invention can be used in a pharmaceutical composition at a dose ranging from 0.01 mg to 1000 mg a day, administered in only one dose once a day or in several doses along the day, for example twice a day. The daily administered dose is advantageously comprises between 5 mg and 500 mg, and more advantageously between 10 mg and 200 mg. However, it can be necessary to use doses out of these ranges, which could be noticed by the person skilled in the art.

The present invention relates also to a method for preparing a compound of formula (I) according to the present invention comprising the following successive steps:

(i) reaction of a compound of the following formula (II):

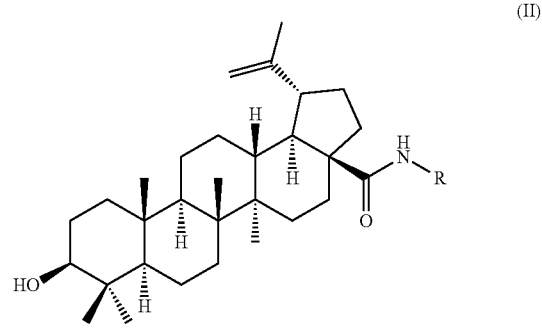

in which R represents a $(C_1-C_{10})$alkyl group substituted with one or more, preferably one or two, groups chosen from COOH and $NHR^1$, with $R^1$ representing a -Alk, —C(O)-Alk or —C(O)O-Alk group, Alk representing a $(C_1-C_6)$alkyl group, with 2,2-dimethylsuccinic anhydride of the following formula:

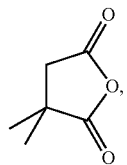

and (ii) optionally, when R comprises a NHR$^1$ group, deprotection of this NHR$^1$ group to yield a NH$_2$ group.

Step (i):

Advantageously, R represents a (C$_1$-C$_6$)alkyl group substituted with one or more, preferably one or two, groups chosen from COOH and NHR$^1$.

R can represent in particular a group —(CHR$^2$)—(CHR$^3$)$_6$—X, in which:

n represents 0 or 1,

X represent a group COOH or NHR$^1$, and

R$^2$ and R$^3$ represent, independently of each other, a hydrogen atom or a (C$_1$-C$_8$)alkyl group, preferably a (C$_1$-C$_4$) alkyl group, optionally substituted with a COOH or NHR$^1$ group.

Preferably, at least R$^2$ or R$^3$ represents a hydrogen atom. In the definition of R above, R$^1$ can represent advantageously a —C(O)O-Alk group such as a Boc group (tert-butyloxycarbonyl).

In particular, R will be chosen from the following groups:

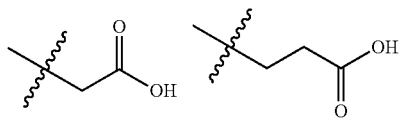

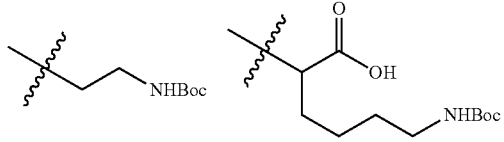

The reaction of step (i) can be carried out in the presence of DMAP (N,N-dimethylaminopyridine) in pyridine, notably at reflux.

The reaction leads to a mixture of 3-O-(2',2'-dimethylsuccinyl)- and 3-O-(3',3'-dimethylsuccinyl)-betulinic acid derivatives. The products of this mixture can be separated by flash chromatography to yield the desired compound of formula (I) (a 3-O-(3',3'-dimethylsuccinyl)-betulinic acid derivative).

Step (ii):

This step of deprotection, if need be, is well-known to the person skilled in the art.

Preferably, the R$^1$ group will be in this case a —C(O)O-Alk group such as a Boc group. The deprotection step of the Boc group can be carried out by first treating the compound with tert-butyldimethylsilyl trifluoromethanesulfonate in the presence of 2,6-lutidine to give a tert-butyldimethylsilyl carbamate, i.e. the group —NHBoc is replaced with a group —NH—C(O)—SiMe$_2$tBu. Then, the removal of the N-tert-butyldimethylsilyloxycarbonyl group can be achieved by treatment with fluoride ions, which can be provided by n-Bu$_4$NF, in a solvent such as THF. Another possibility is to cleave the N-Boc bond in the presence of HCl in a solvent such as THF.

The compound of formula (II) can be prepared by the following successive steps:

(a) coupling between a compound of formula (III)

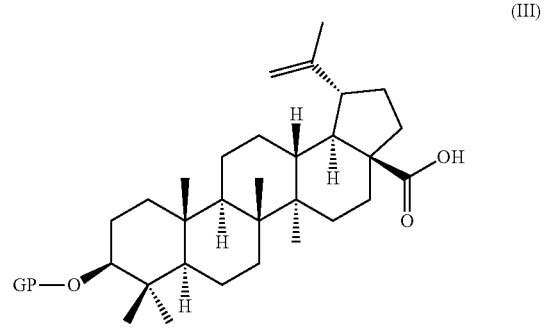

(III)

in which GP represents a O-protecting group such as an acetyl group, with an amine of the following formula (IV):

R$^4$—NH$_2$ (IV)

in which R$^4$ represents a (C$_1$-C$_{10}$)alkyl group substituted with one or more, preferably one or two, groups chosen from —COO-Alk$^1$ and NHR$^1$, with R$^1$ representing a -Alk, —C(O)-Alk or —C(O)O-Alk group, Alk and Alk$^1$ representing, independently from one another, a (C$_1$-C$_6$)alkyl group, to yield a compound of the following formula (IV):

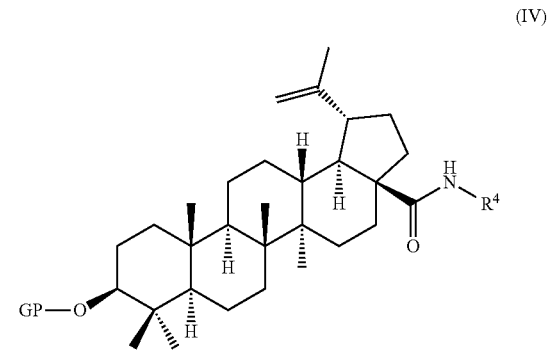

(IV)

in which R$^4$ and GP are as defined above, and (b) deprotection of the hydroxyl group and, when appropriate, the —COO-Alk$^1$ and/or NHR$^1$ group of the compound of formula (IV) obtained in the previous step (a) to yield a compound of formula (II).

Step (a):

Advantageously, R$^4$ represents a (C$_1$-C$_6$)alkyl group substituted with one or more, preferably one or two, groups chosen from COO-Alk$^1$ and NHR$^1$.

R$^4$ can represent in particular a group —(CHR$^2$)—(CHR$^3$)$_n$—X, in which:

n represents 0 or 1,

X represent a group COO-Alk$^1$ or NHR$^1$, and

R$^2$ and R$^3$ represent, independently of each other, a hydrogen atom or a (C$_1$-C$_8$)alkyl group, preferably a (C$_1$-C$_4$) alkyl group, optionally substituted with a COO-Alk$^1$ or NHR$^1$ group.

Preferably, at least $R^2$ or $R^3$ represents a hydrogen atom.

In the definition of $R^4$ above, $R^1$ can represent advantageously a —C(O)O-Alk$^1$ group such as a group Boc (tert-butyloxycarbonyl). Alk$^1$ can represent advantageously a tert-butyl group.

In particular, $R^4$ will be chosen from the following groups:

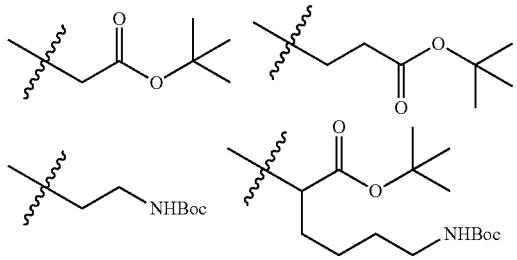

The term "O-Protecting group" as used in the present invention refers to a substituent which protects hydroxyl groups against undesirable reactions during synthetic procedures such as those O-protecting groups disclosed in Greene, "Protective Groups In Organic synthesis", (John Wiley & Sons, New York (1981)). O-protecting groups comprise ($C_1$-$C_6$)alkyl groups, such as methyl, ethyl tert-butyl; substituted methyl ethers, for example, methoxymethyl (MOM), benzyloxymethyl, 2-methoxyethoxymethyl, 2-(trimethylsilyl)ethoxymethyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl (TBS) and t-butyldiphenylsilyl; and esters prepared by reacting the hydroxyl group with a carboxylic acid for example, acetyl, propionyl, benzoyl and the like. It will be in particular an acetyl group.

The coupling can be carried out by a peptide coupling well-known to the person skilled in the art.

The peptide coupling will be advantageously carried out in the presence of a coupling agent, such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), hexafluorophosphate 2-H-benzotriazole-1-yl)-1,1,3,3-tetramethyluronium (HBTU), tetrafluoroborate 2-(1H-benzotriazole-1-yl)-1,1,3,3-tetramethyluronium (TBTU), hexafluorophosphate O-(7-azobenzotriazol-1-yl)-1,1,3,3-tetramethyluronium (HATU) or (benzotriazol-1-yloxy)tripyrrolodinophosphonium hexafluorophosphate (PyBOP); optionally associated with an auxiliary coupling, such as N-hydroxy-succinimide (NHS), N-hydroxy-benzotriazole (HOBt), 3,4-dihydro-3-hydroxy-4-oxo-1,2,3-benzotriazole (HOOBt), 1-hydroxy-7-azabenzotriazole (HAt) or N-hydroxysylfosuccinimide (sulfo NHS).

Advantageously, the peptide coupling will be carried out in the presence of PyBOP and a base such as diisopropylethylamine (DIEA).

The compound of formula (III) can be prepared moreover from betulinic acid, by a protection step of the hydroxyl group.

Preferably, the O-protecting group will be an acetyl group. This group can be introduced on betulinic acid by reaction with acetic anhydride in pyridine.

Step (b):

The step of deprotection of the O-protecting group can be carried out by methods well-known to the person skilled in the art.

In the case where GP represents an acetyl group, the deprotection step can be carried out by saponification, notably in the presence of sodium hydroxide, notably in a solvent such as a mixture of tetrahydrofuran and methanol.

In these reaction conditions, the —COO-Alk$^1$ group is also deprotected to lead to the desired —COOH group.

The invention will be better understood upon reading the following examples and figures, these examples serving solely to illustrate the invention.

FIGURES

FIG. 1A: Amino acid sequence of the wild type CA-SP1-NC domain (SEQ ID NO:1) used to test the interaction with compound 16.

FIG. 1B: 2D 1H-1H NOESY spectra showing the superimposition of the HN-Hα regions of the wild type CA-SP1-NC peptide in absence and in presence of compound 16. The perturbation of the chemical shifts of the peptide by addition of compound 16 are boxed and numbered on the spectra. Spectra were recorded at a pH of 3.8, in H2O/TFE (70/30) and DMSO-d6 (1%) at 293 K. The amino acids undergoing the most important perturbation of their chemical shifts were identified.

FIG. 1C: Histogram reporting the chemical shift perturbation and showing that the perturbation of the chemical shifts is important for residues A366, M367, V370, N372 and I376 in the SP1 region.

Figure 2:
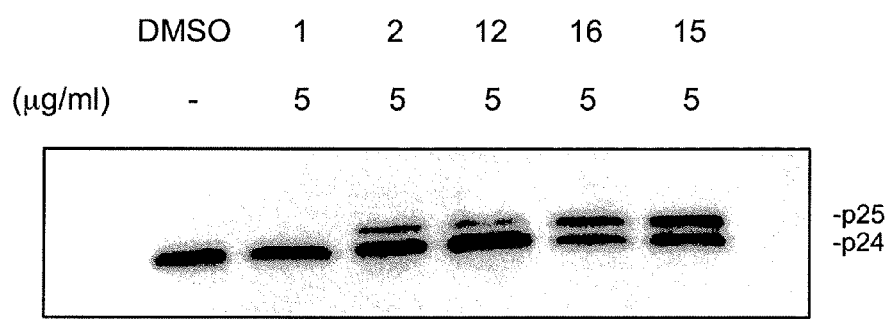

FIG. 2: Effect of compound on virus particle production and Gag processing in virion lysate. The accumulation of p25 is observed in the presence of 1, 2, 12, 16 and 15.

Figure 3:
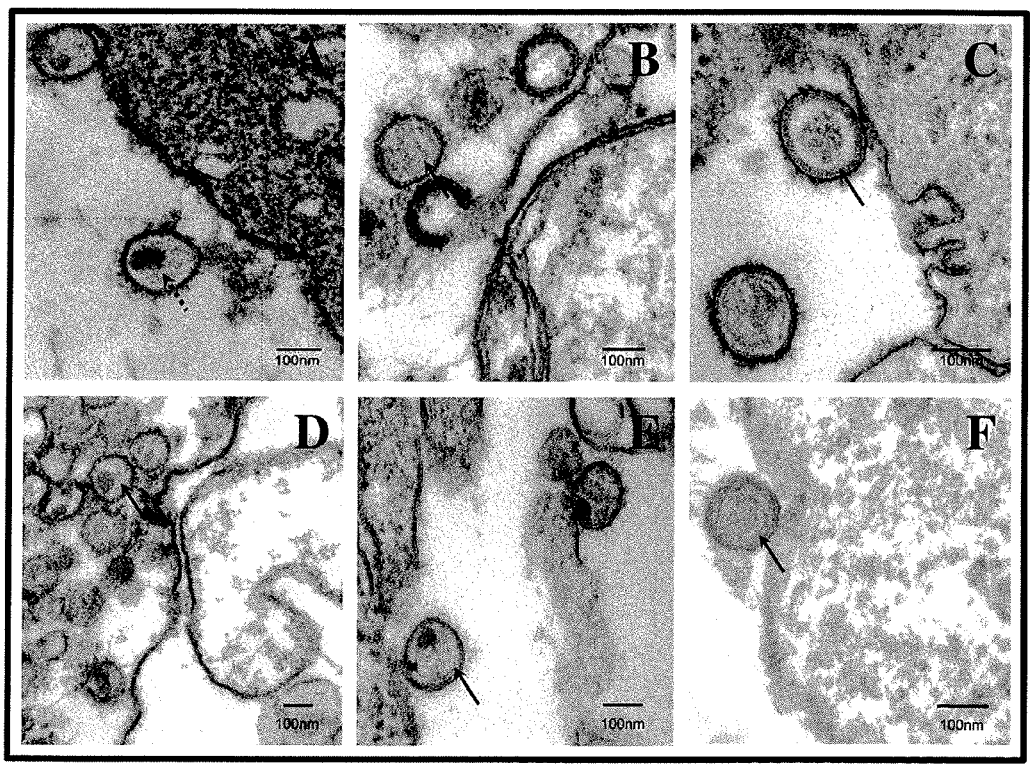

FIG. 3: Thin-section EM analysis of virions produced from BA (1), DSB (2), 12, 16, 15, treated cells.

293T cells were transfected with pNL4-3 and were not treated (A) or treated (B, C, D, E, F) with BA (1), DSB (2), 12, 16 and 15. Two days posttransfection, cells were fixed and analyzed by thin-section EM. Dashed arrow in A indicate mature, conical cores; arrows in B, C, D, E and F indicate the crescent-shaped, electron-dense layer inside the viral membrane that results from inhibition of p25 processing. (Bar: ≈100 nm).

Figure 4:
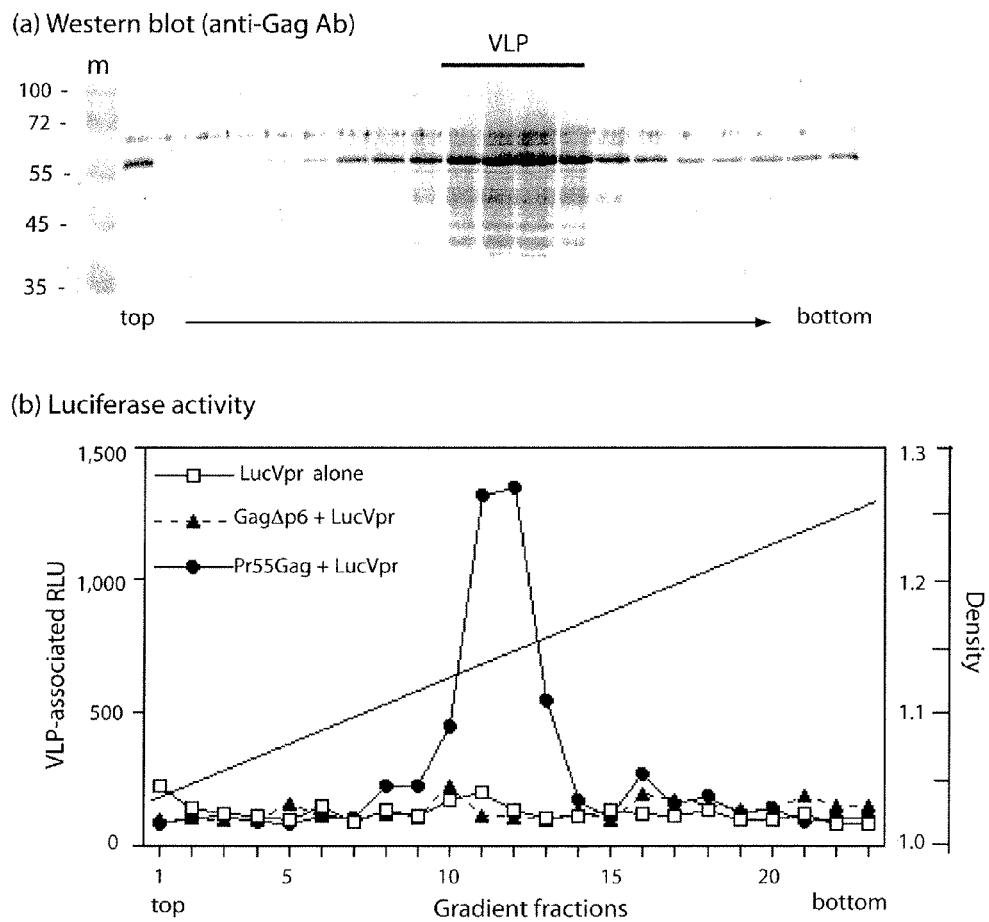

FIG. 4: Gag-p6 domain-dependence of LucVpr packaging.

Isopycnic ultracentrifugation analysis in sucrose-$D_2O$ density gradient of extracellular VLP isolated from Sf9 cell culture medium. (a), Western blot of the gradient fractions analyzed by SDS-PAGE. Blot was reacted with anti-Gag polyclonal antibody and phosphatase-labeled anti-rabbit IgG antibody. Lane m, prestained molecular mass markers (PageRuler™; Fermentas Inc.). The position of VLP (fractions 10-13; 1.12-1.15 in density) is indicated at the top of the panel. (b), Luciferase activity was assayed on each gradient fraction, and expressed as relative light units (RLU). Open symbol, Sf9 cells expressing LucVpr alone; filled symbols, Sf9 cells coexpressing LucVpr and full-length Pr55Gag or p6-deleted Gag (GagΔp6). Each gradient fraction was assayed for luciferase activity. Density values are indicated on the right scale.

Figure 5:
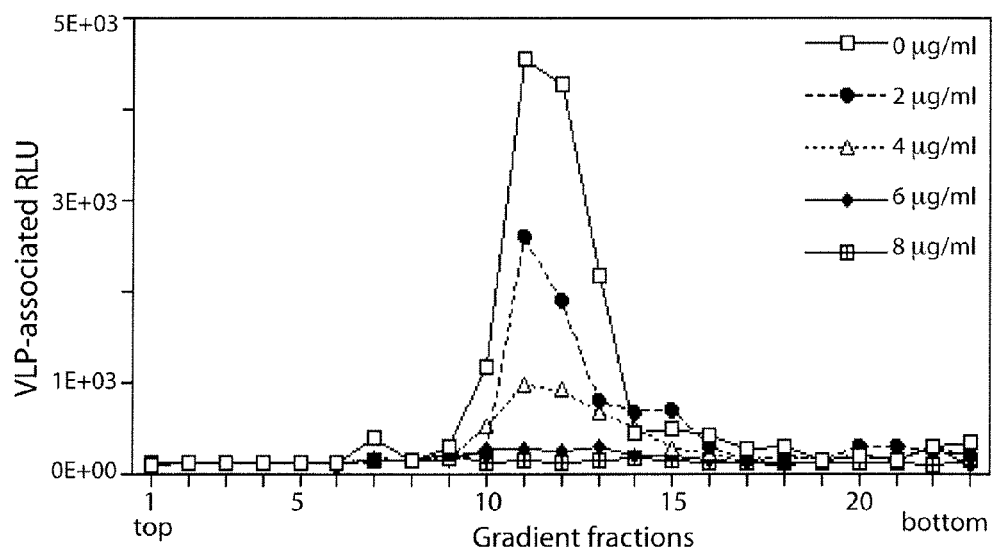

FIG. 5: Quantification of VLP assembly and egress using luciferase assay.

Cells coexpressing Pr55Gag and LucVpr were untreated (control 0) or treated with DSB in DMSO for 24 h at 24 h pi, at increasing concentrations as indicated. VLP were isolated from the culture medium at 48h pi by isopycnic ultracentrifugation in sucrose-$D_2O$ density gradient, and assayed for luciferase activity, expressed as relative light units (RLU).

Figure 6:
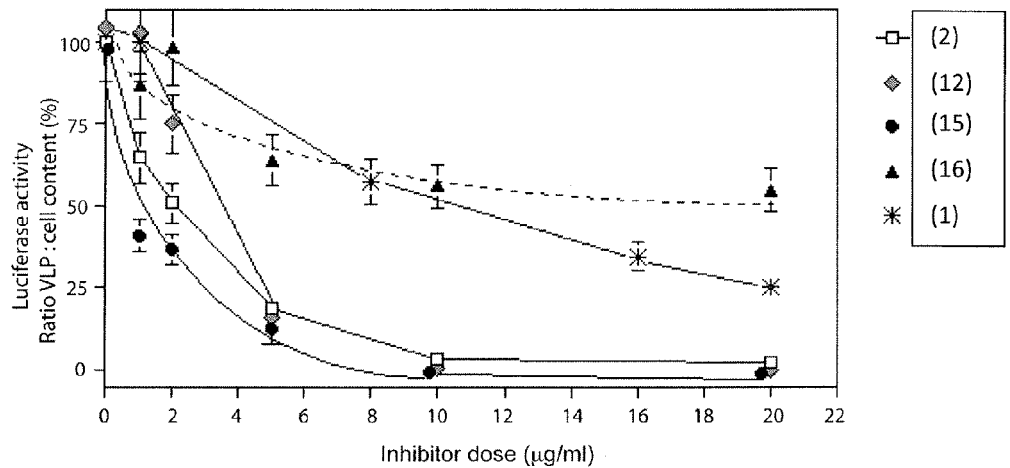

FIG. 6: Evaluation of the inhibitory activity of BA, PA-457, 12, 15 and 16 on VLP assembly, using luciferase-Vpr packaging-based assay.

Aliquots of Sf9 cells coinfected with AcMNPV-Pr55Gag and AcMNPV-LucVpr at equal MOI were treated at 24 h pi with increasing doses of each inhibitor for 24 h. Cells and culture medium were harvested at 48 h pi, and VLP isolated from the culture medium. Cell pellets and VLP were then processed for luciferase assay, and the values of the ratio of VLP-incorporated to cell-associated luciferase activity, in percentage of the control (0 inhibitor), were plotted versus the DSB concentrations. In control samples, the fraction of VLP-incorporated luciferase was usually 5 to 7% of the total activity recovered. E.g., in the experiment illustrated here, the activity recovered was $35.5 \times 10^6$ RLU in cell pellets, versus $2.5 \times 10^6$ in extracellular VLP. Note that the inhibition curve of 17, which resembled that of 12, was not represented for reason of clarity.

EXAMPLES

I. Synthesis of the Compounds According to the Invention

The products were characterized by high resolution mass spectroscopy (HRMS) and by NMR (Nuclear Magnetic Resonance). The IUPAC convention was used for the numbering of the carbon atoms. Complete assignment of the 1H-1 and $^{13}$C NMR resonances was achieved by 1D and 2D NMR experiments, Heteronuclear Single Quantum Correlation (1H,13C-HSQC), Heteronuclear Multi Bond Correlation (1H,13C-HMBC), 1H-1H COrelation SpectroscopY (COSY) and TOtal Corelation SpectroscopY (TOCSY).

1H NMR, 13C NMR, DEPT135, DQF-COSY, TOCSY, HSQC and HMBC spectra were recorded with a Bruker AVANCE 400 NMR spectrometer at 400.13 MHz (SF) for 1H and 100.623 MHz (SF) for 13C with a 5-mm inverse probe at room temperature. The different compounds were 10 mM solutions in 0.5 ml $C_5D_5N$ in 5-mm NMR tubes. All chemical shifts are in ppm ($\delta$). The 1H NMR spectra were performed with spectral width (SW) of 4084.97 Hz and the $^{13}$C NMR spectra with SW of 22522.52 Hz with 1H decoupling with WALTZ pulse sequence; the carbon type (i.e. C, CH, $CH_2$, $CH_3$) was determined by using DEPT135 experiments. All two-dimensional experiments were performed using standard pulse sequences with the Bruker software program XWIN-NMR vs 3.0. DQF-COSY and TOCSY spectra were recorded with 2048 points in the F2 dimension and 512 increments in the F1 dimension. Each increment was obtained with 40 scans a spectral width of 4084.97 Hz, a recycling delay of 2s and a mixing time of 80 ms was used for the TOCSY experiments. The HSQC spectra were obtained with the one-bond 1H-13C coupling constant set to 145 Hz, a GARP 13C decoupling WALTZ, 2048 points in the F2 dimension and 256 increments in the F1 dimension, with a relaxation delay of 2 s. The spectral width was set to 10964.91 Hz in the F2 and 4084.97 Hz in the F1 dimension. The HMBC experiments were performed with 40 scans for each of 256 F1 increments, 2048 data points in F2. A spectral width of 4084.97 Hz and 22522.52 Hz have been used in the 1H and 13C dimensions respectively.

Betulinic acid, acetic anhydride, PyBOP, DIEA, DMAP, 2,2-dimethylsuccinic anhydride, 2,6 lutidine, tert-butyldimethylsilyltrifluoromethanesulfonate were purchased from Aldrich. All amino acids, from Bachem, were O-tBu protected and the side chain of Lys was protected as N-Boc.

The following abbreviations have been used in the experimental part:

$Ac_2O$: acetic anhydride; t-BuMe$_2$SiOTf: tert-butyldimethylsilyltri-fluoromethanesulfonate; nBu$_4$NF: tetrabutylammonium fluoride; DEPT135: Distortionless Enhancement by Polarization Transfer; DIEA: N,N-Diisopropylethylamine; DMAP: 4-(Dimethylamino)pyridine; DMF: Dimethyl-formamide; DMSO: dimethylsulfoxide; DQF-COSY: double quantum filtered-correlation spectroscopy; HMBC: Heteronuclear Multiple Bond Correlation; HSQC: Heteronuclear Single Quantum Correlation; MeOH: methanol; PyBOP: (Benzotriazol-1-yloxy)tripyrrolodinophosphonium hexafluorophosphate; THF: tetrahydrofuran; TOCSY: Total Correlation Spectroscopy.

The compounds have been synthesized according to the following reaction scheme:

Scheme 1$^a$

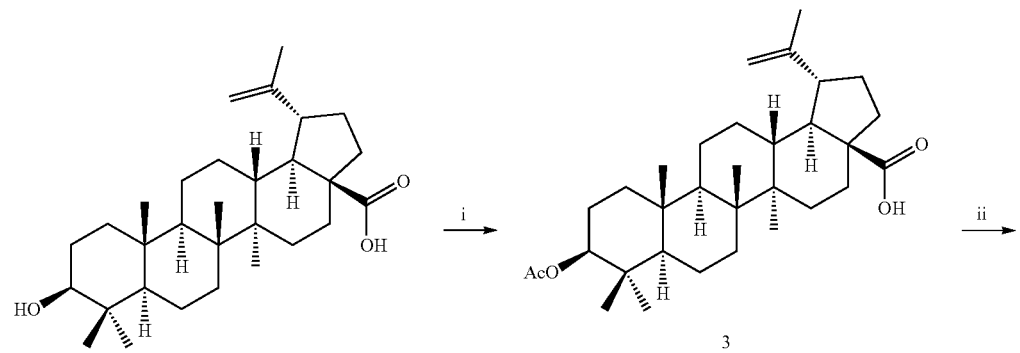

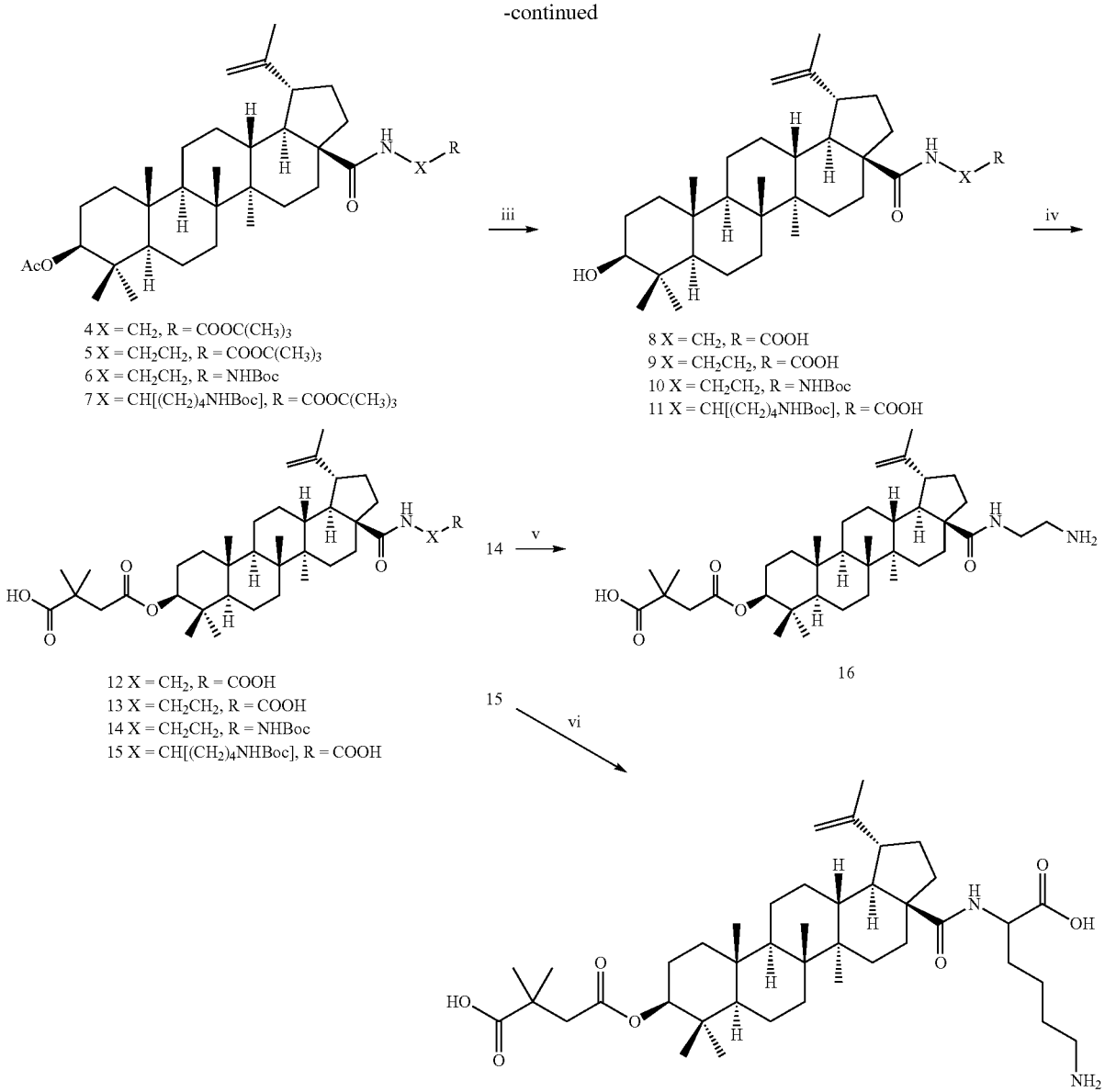

<sup>a</sup>Reagents and conditions: (i) Ac₂O, pyridine; (ii) PyBop, DIEA, NH₂—X—R, rt, 72 h; (iii) NaOH 4M, THF/MeOH, rt, 12 h; (iv) anhydride, DMAP, pyridine, reflux, 18 h; (v) 2,6-lutidine, t-BuMe₂SiOTf, CH₂Cl₂, 30 mn, n-Bu₄NF, THF, rt, 1 h; (vi) HCl 6M, THF, rt, 1 h I.a) General Procedure for Synthesizing Derivatives (4-7).

To a mixture of 3-O—Ac-BA (3) (200-300 mg, 0.4-0.6 mmol) and DIEA (0.28-0.42 mL, 1.6-2.4 mmol) in DMF (2-3 mL) was added successively PyBOP (0.31-0.47 g, 0.6-0.9 mmol) and the appropriate amine NH₂—X—R₁ (0.6-0.9 mmol). The mixture was stirred for 72 h and then diluted with CH₂Cl₂ (50 mL), washed with aqueous citric acid solution (10%), water, brine and dried over MgSO₄. The organic layer was concentrated under vacuum and the residue was purified by silica gel chromatography to provide the desired intermediate 4, 5, 6 or 7.

N—(O³-acetyl-betulinyl)glycine t-butyl ester (4): $R_f$: 0.38 (toluene/acetone 10/0.5); Yield: 64% (158 mg); ¹HNMR (300 MHz, CDCl₃): δ 0.75 (m, 1H, —CH in 5), 0.82 (s, 3H, —CH₃), 0.83 (s, 3H, —CH₃), 0.91 (s, 3H, —CH₃), 0.95 (s, 3H, —CH₃), 1.09 (m, 2H), 1.10-1.45 (m, 11H), 1.47 (s, 12H, —CH₃, t-Bu), 1.50-1.65 (m, 6H), 1.67 (s, 3H, —CH₃), 1.75-2.0 (m, 3H), 2.03 (s, 3H, —COCH₃), 2.45 (dt, 1H, J=3.5 Hz, J=13 Hz), 3.10 (dt, 1H, J=3.5 Hz, J=11 Hz), 3.89 (m, 2H, —CH₂), 4.45 (t, 1H, J=7.5 Hz), 4.58 (s, 1H, =CH), 4.73 (s, 1H, =CH), 6.10 (t, 1H, J=5.2 Hz). ¹³C NMR (300 MHz, CDCl₃): δ 14.6; 16.0; 16.2; 16.5; 18.2; 19.4; 20.9; 21.3; 23.7; 25.5; 27.9; 28.0; 29.4; 30.8; 33.6; 34.3; 36.5; 37.1; 37.6; 37.8; 38.3; 38.4; 40.7; 41.9; 42.5; 45.9; 46.7; 50.0; 50.5; 55.4; 55.7; 80.9; 82.0; 109.4; 150.9; 169.6; 171.0; 176.4.

N—(O³-acetyl-betulinyl)-β-alanine t-butyl ester (5): $R_f$: 0.45 (toluene/acetone 10/0.5); Yield: 80% (300 mg); ¹HNMR (400 MHz, C₅D₅N): δ 0.80 (m, 4H, —CH in 5, —CH₃ in 25), 0.87-0.9 (m, 7H, —CH₃ in 23 and 24, —CH in 1), 1.08 (1s, 3H, —CH₃ in 27), 1.12 (1s, 3H, —CH₃ in 26), 1.18 (m, 1H, —CH in 12), 1.19 (m, 1H, —CH in 11), 1.21 (m, 1H, —CH in 15), 1.33 (m, 1H, —CH in 9), 1.34 (m, 1H, —CH in 11), 1.35 (m, 1H, —CH in 6), 1.42 (m, 2H, —CH in 7), 1.45 (m, 1H, —CH in 6), 1.49 (s, 9H, —COOtBu), 1.5 (m, 1H, —CH in 21), 1.54 (m, 1H, —CH in 22), 1.6 (m, 2H, —CH in 1 and 16), 1.65 (m, 1H, —CH in 2), 1.7 (m, 1H, —CH in 2), 1.74 (m, 1H, —CH in 15), 1.77 (s, 3H, —CH$_3$ in 30), 1.94 (m, 1H, —CH in 12), 2.08 (s, 3H, —COCH$_3$), 2.13 (m, 1H, —CH in 22), 2.21 (m, 1H, —CH in 21), 2.4 (m, 1H, —CH in 16), 2.77 (m, 1H, —CH in 2″), 2.85 (m, 1H, —CH in 2″), 3.08 (m, 1H, —CH in 13), 3.62 (m, 1H, —CH in 19), 3.7 (m, 1H, —CH in 1″), 3.85 (m, 1H, —CH in 1″), 4.7 (dd, 1H, —CH in 3, J=4.5 Hz and 11.5 Hz), 4.78 (s, 1H, =CH), 4.94 (s, 1H, =CH), 8.35 (d, 1H, —CO—NH—. J=7 Hz). $^{13}$C NMR (400 MHz, C$_5$D$_5$N): δ 15.2 (C27); 16.8 (C25); 16.9 (C26); 17.2 (C24); 18.9 (C6); 20 (C30); 21.6 (C2′); 21.66 (C11); 24.5 (C2); 26.6 (C12); 28.5 (3C, t-Bu and C23); 30.3 (C15); 31.8 (C21); 34 (C16); 35.1 (C7); 36.3 (C2″); 36.5 (C1″); 37.7 (C10); 38 (C13); 38.5 (C4); 39 (C22 and C1); 41.6 (C8); 43.2 (C14); 47.65 (C19); 51.1 (C18); 51.3 (C9); 56.1 (C5); 56.3 (C17); 80.7 (Ct-Bu); 81.2 (C3); 110.2 (C29); 152.1 (C20); 171.1 (C1′); 172.4 (C COOt-Bu); 177.4 (C28).

N—(O$^3$-acetyl-betulinyl)-N′-Boc-ethylenediamine (6): R$_f$: 0.48 (toluene/acetone 90/10); Yield: 86% (330 mg); $^1$H NMR (300 MHz, CDCl$_3$): δ 0.77 (m, 1H), 0.83 (s, 3H, —CH$_3$), 0.84 (s, 6H, 2-CH$_3$), 0.94 (s, 3H, —CH$_3$), 0.96 (s, 3H, —CH$_3$), 1.09 (m, 1H), 1.10-1.41 (m, 8H), 1.47 (s, 9H, t-Bu), 1.49-1.65 (m, 8H), 1.68 (s, 3H, —CH$_3$), 1.70-1.80 (m, 3H), 1.98 (m, 3H), 2.04 (s, 3H, —COCH$_3$), 2.45 (dt, 1H, J=3.1 Hz, J=12.5 Hz), 3.13 (dt, 1H, J=4.4 Hz, J=11 Hz), 3.27 (m, 2H, —CH$_2$), 3.34 (m, 2H, —CH$_2$), 4.46 (t, 1H, J=7.0 Hz), 4.59 (s, 1H, =CH), 4.74 (s, 1H, =CH), 5.04 (m, 1H, —NH—CO—), 6.33 (m, 1H, —CO—NH—).

N$^2$—(O$^3$-acetyl-betulinyl)-N$^6$-Boc-L-Lysine t-butyl ester (7): R$_f$: 0.28 (toluene/acetone 95/5); Yield: 73% (410 mg); $^1$H NMR (400 MHz, C$_5$D$_5$N): δ 0.80 (m, 4H, —CH in 5, —CH$_3$ in 25), 0.90 (m, 7H, —CH$_3$ in 23 and 24, —CH in 1), 1.09 (2s, 6H, —CH$_3$ in 27 and 26), 1.16 (m, 1H, —CH in 11), 1.17 (m, 1H, —CH in 12), 1.29 (m, 1H, —CH in 15), 1.32 (m, 1H, —CH in 11), 1.33 (m, 1H, —CH in 9), 1.42 (m, 3H, —CH in 6 and 7), 1.48 (s, 9H, —COOtBu and m, 1H, —CH in 6), 1.52 (m, 2H, —CH in 21 and 22), 1.55 (s, 9H, —NHBoc), 1.58 (m, 2H, —CH in 1 and 2), 1.69 (m, 2H, —CH$_{2γ}$ Lys), 1.70 (m, 3H, —CH in 18, —CH$_{2δ}$ Lys), 1.71 (m, 1H, —CH in 2), 1.78 (s, 3H, —CH$_3$ in 30), 1.80 (m, 1H, —CH in 15), 1.86 (m, 1H, —CH$_β$ Lys), 1.92 (m, 1H, —CH in 12), 2.07 (m, 1H, —CH$_β$ Lys), 2.08 (s, 3H, —COCH$_3$), 2.30 (m, 1H, —CH in 21), 2.33 (m, 1H, —CH in 22), 2.54 (m, 1H, —CH in 16), 3.03 (m, 1H, —CH in 13), 3.40 (m, 2H, —CH$_{2ε}$ Lys), 3.58 (m, 1H, —CH in 19), 4.7 (dd, 1H, —CH in 3, J=5 Hz and 11.5 Hz), 4.75 (s, 1H, =CH), 4.91 (m, 2H, =CH and —CH$_α$ Lys), 7.55 (t, 1H, —NH—CO— J=5 Hz), 8.22 (d, 1H, —CO—NH—. J=8 Hz). $^{13}$C NMR (400 MHz, C$_5$D$_5$N): δ 15.3 (C27); 16.7 (C25); 17 (C26); 17.2 (C24); 19 (C6); 20 (C30); 21.6 (C2′); 21.7 (C11); 24.3 (CγLys); 24.5 (C2); 26.6 (C12); 28.4 (3C, t-Bu); 28.5 (C23); 29 (3C, Boc); 30.3 (C15); 30.5 (CδLys); 31.9 (C21); 32 (CβLys); 34 (C16); 35.1 (C7); 37.8 (C10); 38.1 (C13); 38.5 (C4); 38.65 (C22); 39 (C1); 41.3 (CεLys); 41.6 (C8); 43.2 (C14); 47.6 (C19); 51.1 (C18); 51.3 (C9); 53.4 (CαLys); 56.1 (C5); 56.4 (C17); 78.4 (CBoc); 81.2 (C3); 81.3 (Ct-Bu); 110.2 (C29); 152.1 (C20); 157.25 (C NHCOOt-Bu); 171.1 (C1′); 173.4 (C COOt-Bu); 177.3 (C28).

I.b) General Procedure for Synthesizing Derivatives (8-11).

To the solution of the above intermediate 4, 5, 6 or 7 (0.3 mmol) in THF/MeOH (1/1.4 mL) was added aqueous NaOH (4 M, 0.75 mL). After stirring for 12 h at room temperature, the mixture was acidified with 1N HCl. The resulting precipitate was collected, washed with water and dried over vacuum to yield the corresponding compounds 8 and 9. For compound 10 and 11, the mixture was extracted with CH$_2$Cl$_2$ (50 mL), the organic layer was washed with water, brine and dried over MgSO$_4$ and then concentrated under vacuum. The residue was purified by silica gel chromatography to provide the desired intermediate 8, 9, 10 or 11.

N-betulinyl-glycine (8): Yield: 83% (128 mg); $^1$H NMR (CDCl$_3$): δ 0.70 (m, 1H, —CH in 5), 0.77 (s, 3H, —CH$_3$), 0.83 (s, 3H, —CH$_3$), 0.93 (s, 3H, —CH$_3$), 0.98 (s, 3H, —CH$_3$), 0.99 (s, 3H, —CH$_3$), 1.09 (m, 1H), 1.10-1.65 (m, 20H), 1.70 (s, 3H, —CH$_3$), 1.90 (m, 3H), 2.40 (dt, 1H, J=3.5 Hz, J=13 Hz), 3.10 (dt, 1H, J=3.5 Hz, J=11 Hz), 3.20 (m, 1H), 4.05 (t, 2H, J=7.5 Hz), 4.61 (s, 1H, =CH), 4.75 (s, 1H, =CH), 6.14 (t, 1H, J=5.2 Hz).

N-betulinyl-β-alanine (9): Yield: 89% (141 mg); $^1$H NMR (400 MHz, C$_5$D$_5$N): δ 0.86 (m, 1H, —CH in 5), 0.88 (m, 3H, —CH$_3$ in 25), 0.99 (m, 1H, —CH in 1), 1.04 (s, 3H, —CH$_3$ in 24), 1.08 (s, 3H, —CH$_3$ in 27), 1.16 (s, 3H, —CH$_3$ in 26), 1.2 (m, 1H, —CH in 12), 1.24 (m, 2H, —CH in 11 and —CH in 15), 1.27 (m, 3H, —CH$_3$ in 23), 1.41 (m, 3H, —CH in 6 and —CH in 7), 1.42 (m, 1H, —CH in 9), 1.44 (m, 1H, —CH in 11), 1.5 (m, 2H, —CH in 21 and —CH in 22), 1.58 (m, 2H, —CH in 6 and —CH in 16), 1.68 (m, 1H, —CH in 1), 1.72 (m, 1H, —CH in 18), 1.8 (s, 3H, —CH$_3$ in 30), 1.86 (m, 1H, —CH in 15), 1.89 (m, 2H, —CH in 2), 1.98 (m, 1H, —CH in 12), 2.13 (m, 1H, —CH in 22), 2.28 (m, 1H, —CH in 21), 2.44 (m, 1H, —CH in 16), 2.96 (m, 2H, —CH in 2″), 3.05 (m, 1H, —CH in 13), 3.46 (m, 1H, —CH in 3), 3.65 (m, 1H, —CH in 19), 3.93 (m, 1H, —CH in 1″), 3.98 (m, 1H, —CH in 1″), 4.77 (s, 1H, =CH), 4.93 (s, 1H, =CH), 8.36 (d, 1H, —CO—NH—. J=7 Hz). $^{13}$C NMR (400 MHz, C$_5$D$_5$N): δ 16.2 (C27); 17.8 (C24); 17.86 (C25); 17.92 (C26); 20.2 (C6); 21 (C30); 22.6 (C11); 27.6 (C12); 29.7 (C2); 30 (C23); 31.2 (C15); 32.8 (C21); 35 (C16); 36.2 (C7); 37.4 (C2″); 37.9 (C1″); 38.9 (C10); 39.2 (C13); 40.1 (C22); 40.6 (C1); 40.9 (C4); 42.6 (C8); 44.1 (C14); 48.7 (C19); 52.1 (C18); 52.4 (C9); 57.28 (C17); 57.34 (C5); 79.5 (C3); 110.1 (C29); 153.1 (C20); 177.5 (C3″); 178.1 (C28).

N-betulinyl-N′-Boc-ethylenediamine (10): R$_f$: 0.48 (toluene/acetone 80/20); Yield 67% (210 mg); $^1$H NMR (300 MHz, CDCl$_3$): δ 0.70 (m, 1H, —CH in 5), 0.77 (s, 3H, —CH$_3$), 0.83 (s, 3H, —CH$_3$), 0.94 (s, 3H, —CH$_3$), 0.97 (s, 6H, 2-CH$_3$), 1.09 (m, 1H), 1.10-1.40 (m, 9H), 1.45 (s, 9H, t-Bu), 1.50-1.65 (m, 7H), 1.69 (s, 3H, —CH$_3$), 1.72 (m, 3H), 1.99 (m, 2H), 2.46 (dt, 1H, J=3.5 Hz, J=13 Hz), 3.20 (m, 6H), 3.20 (m, 1H), 4.60 (s, 1H, =CH), 4.74 (s, 1H, =CH), 5.01 (m, 1H, —NH—CO—), 6.33 (m, 1H, —CO—NH—).

N$^2$-betulinyl-N$^6$-Boc-L-Lysine (11): R$_f$: 0.32 (n-heptane/ethyl acetate/acetic acid 10/10/0.25); Yield 97% (277 mg); $^1$H NMR (400 MHz, C$_5$D$_5$N): δ 0.86 (m, 4H, —CH in 5, —CH$_3$ in 25), 1.02 (m, 1H, —CH in 1), 1.06 (s, 3H, —CH$_3$ in 24), 1.10 (s, 3H, —CH$_3$ in 27), 1.18 (s, 3H, —CH$_3$ in 26), 1.20 (m, 1H, —CH in 12), 1.22 (m, 1H, —CH in 11), 1.26 (s, 3H, —CH$_3$ in 23), 1.35 (m, 1H, —CH in 15), 1.42 (m, 1H, —CH in 11), 1.43 (m, 1H, —CH in 9), 1.48 (m, 1H, —CH in 6), 1.50 (m, 2H, —CH$_2$ in 7), 1.52 (m, 1H, —CH in 21), 1.53 (m, 1H, —CH in 22), 1.55 (s, 9H, —NHBoc), 1.61 (m, 1H, —CH in 6), 1.67 (m, 1H, —CH in 16), 1.70 (m, 1H, —CH in 1), 1.75 (m, 1H, —CH in 18), 1.77 (s, 3H, —CH$_3$ in 30), 1.80 (m, 2H, —CH$_{2δ}$ Lys), 1.81 (m, 2H, —CH$_{2γ}$ Lys), 1.88 (m, 2H, —CH$_2$ in 2), 1.91 (m, 1H, —CH in 15), 1.96 (m, 1H, —CH in 12), 2.05 (m, 1H, —CH$_β$ Lys), 2.30 (m, 1H, —CH$_β$ Lys), 2.36 (m, 1H, —CH in 21), 2.45 (m, 1H, —CH in 22), 2.58 (m, 1H, —CH in 16), 3.09 (m, 1H, —CH in 13), 3.43 (m, 2H, —CH$_{2ε}$ Lys), 3.49 (m, 1H, —CH in 3), 3.65 (m, 1H, —CH in 19), 4.77 (s, 1H, —CH in 29), 4.92 (s, 1H, =CH in 29), 5.16 (m, 1H, —CH$_α$ Lys), 7.58 (m, 1H, —NH—CO—), 8.25 (d, 1H, —CO—NH—, J=8 Hz). $^{13}$C NMR (400 MHz, C$_5$D$_5$N): δ 15.3 (C27); 16.85 (C24); 17 (C25); 17.1 (C26); 19.3 (C6); 20 (C30); 21.7 (C11); 24.5 (CγLys); 26.7 (C12); 28.8 (C2); 29.1 (3C, Boc); 29.2 (C23); 30.4 (C15); 30.6 (CδLys); 31.9 (C21); 32.5 (CβLys); 34.2 (C16); 35.4 (C7); 38 (C10); 38.2 (C13); 38.8 (C22); 39.75 (C1); 40 (C4); 41.4 (CεLys); 41.7 (C8); 43.2 (C14); 47.7 (C19); 51.2 (C18); 51.6 (C9); 53 (CαLys); 56.4 (C5); 56.6 (C17); 78.4 (3CBoc); 78.6 (C3); 110.1 (C29); 152.2 (C20); 157.3 (C, NHCOOt-Bu); 176.6 (C, COOH); 177.4 (C28).

I.c) General Procedure for Synthesizing Derivatives (12-15). A Mixture of the Above intermediate 8, 9, 10 or 11, 2,2-dimethylsuccinic anhydride (10 equiv) and DMAP (1 equiv) in anhydrous pyridine (20 mL/mmol) was refluxed overnight. The mixture was then concentrated under vacuum and the residue was chromatographed on Si gel to yield the desired compound 12, 13, 14 or 15.

N-[3β-(3-carboxy-3-methylbutanoyloxy)-lup-20,29-en-28-oyl]-glycine (12): R$_f$: 0.23 dichloromethane/methanol/acetic acid (10/0.1/0.02); Yield 58% (80 mg); HRMS (ESI) calcd for C$_{38}$H$_{58}$NO$_7$ [M-H]$^-$ 640.4219 found 640.4232; $^1$H NMR (400 MHz, C$_5$D$_5$N): δ 0.73 (s, 3H, —CH$_3$ in 25), 0.77 (m, 1H, —CH in 5), 0.89 (m, 1H, —CH in 1), 0.92 (s, 3H, —CH$_3$ in 24), 0.96 (s, 3H, —CH$_3$ in 23), 1.06 (s, 3H, —CH$_3$ in 27), 1.12 (s, 3H, —CH$_3$ in 26), 1.15 (m, 1H, —CH in 12), 1.15 (m, 1H, —CH in 11), 1.26 (m, 1H, —CH in 15), 1.30 (m, 2H, —CH in 9, —CH in 11), 1.30-1.40 (m, 4H, —CH$_2$ in 6, —CH$_2$ in 7), 1.52 (m, 1H, —CH in 1), 1.54 (m, 1H, —CH in 21), 1.55 (s, 3H, —CH$_3$ in 5'), 1.59 (m, 1H, —CH in 22), 1.67 (m, 2H, —CH in 2, —CH in 16), 1.74 (m, 1H, —CH in 18), 1.77 (m, 1H, —CH in 2), 1.78 (s, 3H, —CH$_3$ in 30), 1.93 (m, 1H, —CH in 12), 2.03 (m, 1H, —CH in 15), 2.38 (m, 1H, —CH in 21), 2.39 (m, 1H, —CH in 22), 2.59 (m, 1H, —CH in 16), 2.91 (d, 1H, —CH in 2', J=15.5 Hz), 2.95 (d, 1H, —CH in 2', J=15.5 Hz), 3.08 (m, 1H, —CH in 13), 3.66 (m, 1H, —CH in 19), 4.44-4.51 (dd, 2H, —CH$_2$ in 1", J=6 Hz, J=17.5 Hz), 4.75 (s, 1H, —CH in 29), 4.77 (d, 1H, —CH in 3, J=5 Hz), 4.96 (s, 1H, —CH in 29), 8.76 (t, 1H, —NH—CO—, J=5.5 Hz). $^{13}$C NMR (400 MHz, C$_5$D$_5$N): δ 15.3 (C27); 16.7 (C25); 17 (C26); 17.3 (C24); 18.9 (C6); 20 (C30); 21.6 (C11); 24.6 (C2); 26.6 (C12); 26.7 (C5'); 28.5 (C23); 30.3 (C15); 31.8 (C21); 34 (C16); 35 (C7); 37.7 (C10); 38.1 (C13); 38.5 (C4); 39 (C1); 39.1 (C22); 41.3 (C3'); 41.6 (C8); 42.4 (C1"); 43.2 (C14); 45.6 (C2'); 47.7 (C19); 51.0 (C18); 51.2 (C9); 56.0 (C5); 56.4 (C17); 81.4 (C3); 110.3 (C29); 152.2 (C20); 172.1 (C1'); 174 (C6"); 177.9 (C28); 179.8 (C4').

N-[3β-(3-carboxy-3-methylbutanoyloxy)lup-20,29-en-28-oyl]-β-alanine (13): R$_f$: 0.27 n-heptane/ethyl acetate/acetic acid (10/10/0.5); Yield 2.62% (166 mg); HRMS (ESI) calcd for C$_{39}$H$_{60}$NO$_7$ [M-H]$^-$ 654.4375 found 654.4375, calcd for C$_{39}$H$_{59}$NO$_7$Na [M-2H+Na]$^-$ 676.4195 found 676.4186; $^1$H NMR (400 MHz, C$_5$D$_5$N): δ 0.74 (m, 1H, —CH in 5 and s, 3H, —CH$_3$ in 25), 0.91 (m, 1H, —CH in 1), 0.94 (s, 3H, —CH$_3$ in 24), 0.97 (s, 3H, —CH$_3$ in 23), 1.04 (s, 3H, —CH$_3$ in 27), 1.08 (s, 3H, —CH$_3$ in 26), 1.17 (m, 2H, —CH in 11 and —CH in 12), 1.2 (m, 1H, —CH in 15), 1.30 (m, 2H, —CH in 9, —CH in 6), 1.31 (m, 1H, —CH in 11), 1.33 (m, 2H, —CH in 7), 1.4 (m, 1H, —CH in 6) 1.52 (m, 2H, —CH in 21 and —CH in 22), 1.55 (s, 3H, —CH$_3$ in 5'), 1.58 (m, 2H, —CH in 1 and —CH in 16), 1.7 (m, 2H, —CH in 18 and —CH in 2), 1.81 (s, 3H, —CH$_3$ in 30), 1.82 (m, 1H, —CH in 2), 1.85 (m, 1H, —CH in 15), 1.96 (m, 1H, —CH in 12), 2.16 (m, 1H, —CH in 22), 2.27 (m, 1H, —CH in 21), 2.47 (m, 1H, —CH in 16), 2.94 (d, 1H, —CH in 2', J=15.5 Hz), 3.00 (d, 1H, —CH in 2', J=15.5 Hz), 3.01 (m, 1H, —CH in 2"), 3.07 (m, 1H, —CH in 13), 3.67 (m, 1H, —CH in 19), 3.9 (m, 1H, —CH$_2$ in 1"), 4.03 (m, 1H, —CH$_2$ in 1") 4.79 (m, 2H, —CH in 3 and —CH in —29), 4.97 (s, 1H, —CH in 29), 8.33 (t, 1H, —NH—CO—, J=7 Hz). $^{13}$C NMR (400 MHz, C$_5$D$_5$N): δ 15.2 (C27); 16.7 (C25); 16.9 (C26); 17.4 (C24); 18.9 (C6); 20 (C30); 21.7 (C11); 24.6 (C2); 26.6 (C12); 26.7 (C5'); 28.6 (C23); 30.3 (C15); 31.8 (C21); 34 (C16); 35 (C7); 35.7 (C2"); 36.7 (C1"); 37.7 (C10); 38.2 (C13); 38.5 (C4); 39 (C1); 39.1 (C22); 41.3 (C3'); 41.6 (C8); 43.2 (C14); 45.7 (C2'); 47.7 (C19); 51.1 (C18); 51.2 (C9); 56.1 (C5); 56.3 (C17); 81.4 (C3); 110.2 (C29); 152.2 (C20); 172 (C1'); 175.4 (C6"); 177.2 (C28); 179.8 (C4').

N—[O$^3$-(3-carboxy-3-methylbutylyl)betulinyl]-N'-Boc-ethylenediamine (14): R$_f$: 0.25 dichloromethane/methanol/acetic acid (10/0.2/0.01); Yield 82% (190 mg); $^1$H NMR (300 MHz, CDCl$_3$): δ 0.72 (m, 1H, —CH in 5), 0.77 (s, 3H, —CH$_3$), 0.78 (s, 3H, —CH$_3$), 0.79 (s, 3H, —CH$_3$), 0.89 (s, 3H, —CH$_3$), 0.92 (s, 3H, —CH$_3$), 1.10 (m, 1H), 1.26 (s, 6H), 1.27-1.40 (m, 6H), 1.42 (s, 9H, t-Bu), 1.42-1.63 (m, 7H), 1.69 (s, 3H, —CH$_3$), 1.72 (m, 2H), 1.99 (m, 2H), 2.46 (m, 1H), 2.57 (m, 2H), 3.08 (m, 1H), 3.31 (m, 9H), 4.42 (m, 1H), 4.55 (s, 1H, =CH), 4.69 (s, 1H, =CH), 5.17 (m, 1H, —NH—CO—), 5.28 (m, 1H, —CO—NH—).

N$^2$—[O$^3$-(3-carboxy-3-methylbutyryl)betulinyl]-N$^6$-Boc-L-lysine (15): R$_f$: 0.31 n-heptane/ethyl acetate/acetic acid (10/10/0.25); Yield 36% (106 mg); HRMS (ESI) calcd for C$_{47}$H$_{75}$N$_2$O$_7$ [M-H]$^-$ 811.5478 found 811.5476; $^1$H NMR (400 MHz, C$_5$D$_5$N): δ 0.76 (s, 3H, —CH$_3$ in 25), 0.82 (m, 1H, —CH in 5), 0.9 (m, 1H, —CH in 1), 0.96 (s, 3H, —CH$_3$ in 24), 0.97 (s, 3H, —CH$_3$ in 23), 1.08 (s, 3H, —CH$_3$ in 27), 1.09 (s, 3H, —CH$_3$ in 26), 1.15 (m, 2H, —CH in 12 and —CH in 11), 1.3 (m, 1H, —CH in 9), 1.32 (m, 1H, —CH in 15), 1.33 (m, 1H, —CH in 11), 1.36-1.46 (m, 4H, —CH$_2$ in 6, —CH$_2$ in 7), 1.53 (m, 1H, —CH in 21), 1.54 (m, 1H, —CH in 22), 1.55-1.59 (s, 3H, —CH$_3$ in 5' and s, 9H, —NHBoc and m, 1H, —CH in 1), 1.67-1.7 (m, 2H, —CH in 2, —CH in 16), 1.73 (m, 1H, —CH in 18), 1.78 (m, 1H, —CH in 2), 1.78 (s, 3H, —CH$_3$ in 30), 1.8 (m, 2H, —CH$_{2ε}$ Lys), 1.83 (m, 1H, —CH$_{2δ}$ Lys), 1.89 (m, 1H, —CH in 15), 1.95 (m, 1H, —CH in 12), 2.06 (m, 1H, —CH$_{2β}$ Lys), 2.3 (m, 1H, —CH$_{2β}$ Lys), 2.34 (m, 1H, —CH in 21), 2.43 (m, 1H, —CH in 22), 2.58 (m, 1H, —CH in 16), 2.9 (d, 1H, —CH in 2', J=15.5 Hz), 2.98 (d, 1H, —CH in 2', J=15.5 Hz), 3.07 (m, 1H, —CH in 13), 3.43 (m, 2H, —CH$_{2ε}$ Lys), 3.63 (m, 1H, —CH in 19), 4.77 (s, 1H, —CH in 29), 4.78 (dd, 1H, —CH in 3, J=5 Hz and J=11.5 Hz), 4.92 (s, 1H, —CH in 29), 5.17 (m, 1H, —CH$_α$ Lys), 7.58 (m, 1H, —NH—CO—O), 8.26 (d, 1H, —CO—NH—, J=8 Hz). $^{13}$C NMR (400 MHz, C$_5$D$_5$N): δ 15.3 (C27); 16.7 (C25); 17 (C26); 17.4 (C24); 19 (C6); 20.0 (C30); 21.7 (C11); 24.5 (CγLys); 24.6 (C2); 26.4 (C5'); 26.6 (C12); 28.6 (C23); 29.1 (3C, Boc); 30.3 (C15); 30.6 (CδLys); 31.9 (C21); 32.4 (CβLys); 34.2 (C16); 35.1 (C7); 37.75 (C10); 38.1 (C13); 38.5 (C4); 38.8 (C22); 39 (C1); 41.3 (C3'); 41.4 (CεLys); 41.6 (C8); 43.2 (C14); 45.7 (C2'); 47.7 (C19); 51.1 (C18); 51.2 (C9); 53 (CαLys) 56.1 (C5); 56.5 (C17); 78.4 (COBoc); 81.4 (C3); 110.2 (C29); 152.2 (C20); 172.1 (C1'); 176.6 (C6"); 177.7 (C28); 179.8 (C4').

I.d) Procedure for the Synthesis of Compound 16. To a stirred solution under argon of N-t-Boc derivative 14 (0.19 mg, 0.26 mmol) and 2,6 lutidine (91 μL, 0.78 mmol) in dry CH$_2$Cl$_2$ (1 mL) was added dropwise tert-butyldimethylsilyl-trifluoromethanesulfonate (t-BuMe2SiOTf, 150 μL, 0.65 mmol). The reaction mixture was stirred 30 min, quenched with saturated aqueous ammonium chloride solution (2 mL). The mixture was diluted with CH$_2$Cl$_2$ (5 mL), the organic layer was washed with water, brine and dried over MgSO$_4$. The solvent was concentrated under vacuum and the residue was used in the next step without purification.

To a stirred solution of the N-(tert-butyldimethylsilyloxycarbonyl) derivative in dry THF (0.5 mL) at room temperature was added tetrabutylammonium fluoride (260 µL, 1 M solution in THF, 0.26 mmol). The reaction mixture was stirred for 1 h, quenched with saturated aqueous ammonium chloride solution (2 mL). The resulting precipitate was collected, washed with water and dried over vacuum to yield the corresponding compound 16.

4-({28-[(2-aminoethyl)amino]-28-oxolup-20,29-en-3β-yl}oxy)-2,2-dimethyl-4-oxobutanoic acid (16): Yield: 26% (45 mg); HRMS (ESI) calcd for $C_{38}H_{61}N_2O_5$ [M-H]⁻ 625.4586 found 625.4569; ¹H NMR (400 MHz, $C_5D_5N$): δ 0.75 (s, 3H, —$CH_3$ in 25), 0.77 (m, 1H, —CH in 5), 0.86 (m, 1H, —CH in 1), 0.93 (s, 3H, —$CH_3$ in 24), 0.97 (s, 3H, —$CH_3$ in 23), 1.03 (s, 3H, —$CH_3$ in 27), 1.03 (s, 3H, —$CH_3$ in 26), 1.12 (m, 1H, —CH in 12), 1.13 (m, 1H, —CH in 11), 1.17 (m, 1H, —CH in 15), 1.30 (m, 2H, —CH in 9, —CH in 11), 1.30-1.40 (m, 4H, —$CH_2$ in 6, —$CH_2$ in 7), 1.48 (m, 1H, —CH in 21), 1.54 (m, 1H, —CH in 1), 1.55 (s, 3H, —$CH_3$ in 5'), 1.55 (m, 1H, —CH in 22), 1.64-1.67 (m, 2H, —CH in 2, —CH in 16), 1.70 (m, 2H, —CH in 15, —CH in 18), 1.77 (m, 1H, —CH in 2), 1.77 (s, 3H, —$CH_3$ in 30), 1.92 (m, 1H, —CH in 12), 2.14 (m, 1H, —CH in 21), 2.25 (m, 1H, —CH in 22), 2.67 (m, 1H, —CH in 16), 2.90 (d, 1H, —CH in 2', J=15.5 Hz), 2.96 (d, 1H, —CH in 2', J=15.5 Hz), 3.03 (m, 1H, —CH in 13), 3.28 (m, 2H, —$CH_2$ in 2"), 3.61 (m, 1H, —CH in 19), 3.87-3.81 (m, 2H, —$CH_2$ in 1"), 4.75 (s, 1H, —CH in 29), 4.77 (d, 1H, —CH in 3, J=5 Hz), 4.93 (s, 1H, —CH in 29), 8.74 (m, 1H, —NH—CO—). ¹³C NMR (400 MHz, $C_5D_5N$): δ 15.2 (C27); 16.7 (C25); 16.9 (C26); 17.4 (C24); 19 (C6); 20.0 (C30); 21.6 (C11); 24.6 (C2); 26.5 (C12); 26.7 (C5'); 28.5 (C23); 30.3 (C15); 31.8 (C21); 34.0 (C16); 35.0 (C7); 37.7 (C10); 38.1 (C13); 38.5 (C4); 39.0 (C22); 39.1 (C1); 41.0 (C1"); 41.4 (C3'); 41.5 (C8); 42.2 (C2"); 43.1 (C14); 45.7 (C2'); 47.7 (C19); 51.2 (C18); 51.3 (C9); 56.1 (C5); 56.5 (C17); 81.3 (C3); 110.2 (C29); 152.2 (C20); 172.1 (C1'); 177.7 (C28); 179.9 (C4').

I.e) Procedure for the Synthesis of Compound 17. The N-Boc protection of product 15 was cleaved with HCl 6N in THF for one hour. Compound 17 was obtained after purification by flash chromatography.

$N^2$-[3β-(3-carboxy-3-methylbutanoyloxy)lup-20,29-en-28-oyl]-L-lysine (17): Yield: 45% (20 mg); HRMS (ESI) calcd for $C_{42}H_{67}N_2O_7$ [M-H]⁻ 711.4954 found 711.4960; ¹H NMR (400 MHz, $CD_3OD$): δ 0.82 (m, 1H, —CH in 5), 0.85 (s, 3H, —$CH_3$ in 24), 0.87 (s, 3H, —$CH_3$ in 23), 0.92 (s, 3H, —$CH_3$ in 25), 0.96 (s, 3H, —$CH_3$ in 26), 0.99 (m, 1H, —CH in 1), 1.01 (s, 3H, —$CH_3$ in 27), 1.04 (m, 1H, —CH in 12), 1.18 (m, 1H, —CH in 15), 1.25 (s, 3H, —$CH_3$ in 5'), 1.26 (m, 1H, —CH in 11), 1.35 (m, 1H, —CH in 21), 1.36 (m, 1H, —CH in 9), 1.38-1.52 (m, 9H, —$CH_2$ in 6, —$CH_2$ in 7, —CH in 11, —CH in 15, —CH in 22, —$CH_2$ in 3"), 1.56 (m, 1H, —CH in 16), 1.6 (m, 1H, —CH in 2), 1.64 (m, 1H, —CH in 18), 1.68 (m, 1H, —CH in 2), 1.7 (m, 6H, —$CH_3$ in 30, —CH in 12, 2H, —$CH_2$ in 4"), 1.72 (m, 1H, —CH in 1), 1.75 (m, 1H, —CH in 2"), 1.89 (m, 1H, —CH in 2"), 1.9 (m, 1H, —CH in 21), 1.93 (m, 1H, —CH in 22), 2.17 (m, 1H, —CH in 16), 2.53 (m, 1H, —CH in 13), 2.55 (d, 1H, —CH in 2', J=15.5 Hz), 2.62 (d, 1H, —CH in 2', J=15.5 Hz), 2.90 (t, 2H, —CH in 5", J=8 Hz), 3.06 (m, 1H, —CH in 19), 4.3 (m, 1H, —CH in 1"), 4.44 (dd, 1H, —CH in 3, J=5 Hz and J=10 Hz), 4.57 (s, 1H, —CH in 29), 4.7 (s, 1H, —CH in 29), 7.1 (m, 1H, —NH—CO—). ¹³C NMR (400 MHz, $CD_3OD$): δ 15.2 (C27); 17 (C25); 17.1 (C26); 17.2 (C24); 19.4 (C6); 19.8 (C30); 22.3 (C11); 24.05 (C3"); 24.8 (C2); 26.2 (C5'); 27.2 (C12); 28.2 (C4"); 28.7 (C23); 30.9 (C15); 32.1 (C21); 32.7 (C2"); 34.4 (C16); 35.7 (C7); 38.4 (C10); 39 (C4); 39.2 (C13); 39.3 (C22); 39.8 (C1); 40.7 (C5"); 41.5 (C3'); 42.2 (C8); 43.7 (C14); 45.8 (C2'); 48.3 (C19); 51.4 (C18); 52.1 (C9); 54 (C1"); 57 (C5); 57.4 (C17); 82.8 (C3); 110.2 (C29); 152.4 (C20); 173.1 (C1'); 177.3 (C6"); 178.9 (C28); 180.8 (C4').

II. Biological Assays

Materials and Methods

Infection Inhibition Assays.

The evaluation of HIV-1 inhibition was carried out using MAGIC-5B indicator cells, which stably express the β-galactosidase reporter gene cloned downstream of the HIV-1 LTR promoter. Cells were plated at $8 \times 10^4$ cells per well, in 24-well plates and exposed to HIV-1 (x ng p24). Forty-eight hours post-infection, viral infectivity was monitored by quantification of o-nitrophenyl β-D-galactopyranoside hydrolysis from cell lysates (kit). β-galactosidase activity was normalized according to total protein content in the cell lysate. Control wells containing virus and cells only (no drug) and cells only (no virus or drug) were also prepared.

The 50% infection inhibition (IC50) was defined as the concentration of the compound which reduced the HIV-1 infection level by 50% compared to the untreated controls (Table 1).

Cytotoxicity.

The cellular toxicity of the different compounds was evaluated using the MTT assays. The 50% cytotoxic concentration ($CC_{50}$) was defined as the concentration of the compounds which reduced the cell viability by 50% compared to that for the untreated controls. The selectivity index (SI) was defined as the ratio $CC_{50}$: $IC_{50}$ (Table 1).

Electron Microscopy Analysis.

293T cells were transfected in presence or absence of BA, DSB, 12, 15 and 16 (5 µg/ml) with HIV-1 molecular clones (pNL4-3) using the JetPei transfection reagent (QBiogen). Two days after transfection, 293T cells were processed for thin-layer electron microscopy as follows: cells were fixed in situ with 2.5% glutaraldehyde in cacodylate buffer (pH 7.4) for 60 min at 4° C. Cells were then post-fixed with 2% osmium tetroxide, washed in cacodylate buffer containing 0.5% tanic acid, and embedded in epon (Embed-812, Electron Microscopy Sciences Inc.). Sections were counter-stained with uranyl acetate and lead citrate and examined with an Hitachi H7100 transmission electron microscope.

HIV-1 Maturation Inhibition Assay.

Viruses were produced by transfection of HIV-1 molecular clones (pNL4-3) in 293T cells maintained in presence or absence of compounds BA, DSB, 12, 15 and 16 in DMSO using the JetPei transfection reagent (QBiogen). Two days after transfection, virus-containing supernatants were concentrated by ultracentrifugation through a layer of 20% sucrose at 25 000 rpm for 2 h30. Viral pellets were then resuspended in RIPA lysis buffer [10 mM Tris-HCl (pH 7.4), 1 mM EDTA, 100 mM NaCl, 1% Triton X-100, 0.1% SDS, 0.25% sodium deoxycholate, 0.2% phenylmethylsulfonyl fluoride (PMSF)]. Viral proteins were loaded on a 12.5% SDS-PAGE gel. Proteins transferred to PVDF membrane (Millipore) were revealed using a goat antibody anti-HIV CAp24 serum (AbD Serotec). Secondary antibody conjugated to horseradish peroxidase was revealed by enhanced chemiluminescent detection (Pierce Biotechnology, Inc).

Cells and Recombinant Baculoviruses.

(i) Insect Cells. *Spodoptera frugiperda* Sf9 cells were maintained as monolayers, and infected with recombinant baculoviruses at a multiplicity of infection (MOI) ranging from 5 to 10 PFU/cell, as previously described [1,2].

(ii) Gag Clones. The HIV-1 gag gene, as well as the luciferase-vpr fusion gene, used in the present study were inserted into the genome of *Autographa californica* MultiCapsid NucleoPolyhedrosis Virus (AcMNPV) under the control of a chimeric AcMNPV-GmMNPV polyhedrin promoter, and the phenotypes of recombinant Gag proteins described in detail in previous studies [1,2]. AcMNPV-Pr55Gag expressed the full-length wild type (WT) Gag polyprotein (Pr55Gag). The recombinant expressing the N-myristoylated version of the deletion mutant lacking the p6 carboxy-terminal domain, referred to as AcMNPV-GagΔp6(myr+) in previous studies [3] was simply referred to as AcMNPV-GagΔp6 for reason of acronym simplification. In AcMNPV-GagA364V mutant, the first residue of the SP1 domain, alanine, was mutated into valine, using the conventional PCR overlapping method. GagA364V is the prototype of mutants resistant to DSB inhibition of Gag processing [4].

(iii) Vpr. The baculovirus clone expressing the oligohistidine-tagged Vpr protein (AcMNPV-Vpr) was obtained from Nathaniel Landau via Eric Cohen [5].

(iv) Luciferase-Vpr fusion construct (LucVpr). The plasmid carrying the vpr gene (LAI isolate) was obtained from Serge Benichou [6]. The firefly (*Photinus pyralis*) luciferase gene sequence was isolated by PCR from the pGL2 plasmid (control plasmid Cat # E1611; Promega). After deletion of its stop codon, a sequence coding for a 6-histidine tag (SEQ ID NO:2) and a GSGS linker (SEQ ID NO:3) was inserted at its 3'-end, and fused to the 5'-end of the vpr gene. The detail of this construct will be communicated upon request. The final fusion construct luc(his)$_6$-vpr was inserted into AcMNPV to generate the AcMNPV-LucVpr recombinant. Of note, the reverse gene fusion vpr-3'-luc(his)$_6$ was also constructed, but the VprLuc fusion protein was found to be incapable of copackaging with Pr55Gag into VLP. (iii) Vpr. The baculovirus clone expressing the oligohistidine-tagged Vpr protein (AcMNPV-Vpr) was obtained from Nathaniel Landau via Eric Cohen.

(iv) Luciferase-Vpr fusion construct (LucVpr). The plasmid carrying the vpr gene (LAI isolate) was obtained from Serge Benichou. The firefly (*Photinus pyralis*) luciferase gene sequence was isolated by PCR from the pGL2 plasmid (control plasmid Cat # E1611 ; Promega). After deletion of its stop codon, a sequence coding for a 6-histidine tag (SEQ ID NO:2) and a GSGS linker (SEQ ID NO:3) was inserted at its 3'-end, and fused to the 5'-end of the vpr gene. The final fusion construct luc(his)$_6$-vpr was inserted into AcMNPV to generate the AcMNPV-LucVpr recombinant.

Isolation of Extracellular Virus-Like Particles (VLP).

Sf9 cell culture supernatants were clarified by low-speed centrifugation, then VLP recovered using a two-step procedure comprising a sucrose-step gradient centrifugation [7], followed by an ultracentrifugation in linear D$_2$O-sucrose gradient [8,9]. (i) In the first step, VLP contained in the cell culture medium were pelleted through a sucrose cushion (20%, w:v, in TNE buffer; TNE: 100 mM NaCl, 10 mM Tris-HCl pH 7.4, 1 mM Na$_2$EDTA) at 30 krpm for 1 h at 15° C. in a Kontron TST55.5 rotor [8]. Pelleted VLP of step (i) were then gently resuspended in PBS (0.20-0.25 ml), and (ii) further analyzed by isopycnic ultracentrifugation in sucrose-D$_2$O gradients [8,9]. Linear gradients (10-ml total volume, 30-50%, w:v) were centrifuged for 18 h at 28 krpm in a Beckman SW41 rotor. The 50% sucrose solution was made in D$_2$O buffered to pH 7.2 with NaOH, and the 30% sucrose solution was made in 10 mM Tris-HCl, pH 7.2, 150 mM NaCl, 5.7 mM Na$_2$EDTA. Aliquots of 0.5 ml were collected from the top, and fractions analyzed for protein content by SDS-PAGE and immunoblotting, and by luciferase assay as described below.

Gag Assembly Inhibition Assays.

Aliquots of Sf9 cells ($10^6$) were infected with two recombinant baculoviruses at equal multiplicity of infection (MOI of 10 PFU/cell, each). One expressed the HIV-1 Gag precursor (AcMNPV-Pr55Gag or control, p6-deleted AcMNPV-GagΔp6), the other the control Vpr protein (AcMNPV-Vpr) or the LucVpr fusion (AcMNPV-LucVpr). At 24 h postinfection (pi), increasing quantities of PA-457, 12, 16 or 15 in DMSO were added to the infected cell cultures. To avoid any interference with a possible effect of DMSO, DMSO was kept constant in volume in the different samples. In standard experiments, stock solutions of PA-457, 12, 16 or 15 (10 mg/ml in DMSO) were diluted with DMSO to obtain a range of inhibitor concentrations from 0.5 to 20 µg per 2 µl-aliquot of DMSO, and each 2 µl-aliquot was added per 1 ml-volume of culture medium overlaying cell monolayers. Cells were harvested at 48 h pi, and extracellular VLP released in the culture medium were quantitated using luciferase assay. Membrane-enveloped VLP were pelleted and resuspended in lysis KDT buffer (KDT: 0.1M potassium phosphate buffer, pH 7.8, 1 mM DTT, containing 0.2% Triton X100) for 30 min at 37° C. with vortexing every 10 min. Luciferase activity associated with VLP was measured as previously described [10], using a Lumat LB-9501 luminometer (Berthold Technologies, Bad Wildbad, Germany). Of note, final concentrations of Triton X100 higher than 0.2% in samples were found to have a detrimental effect on the luciferase enzymatic activity. To compensate for eventual negative effects of drugs on LucVpr expression, the luciferase activity was measured in the corresponding cell lysates, obtained after lysis of the pelleted cells with KDT buffer. The results were expressed as relative light units (RLU) per µg protein. The values of the ratio of VLP-associated to intracellular luciferase activity were plotted versus the inhibitor concentration. The 50% inhibitory concentration (IC$_{50}$) was defined as the compound concentration required to reduce this ratio by 50%, compared to the ratio obtained with untreated cells which was attributed the 100% value.

Cytotoxicity Assays.

The cellular toxicity of the different compounds was evaluated using the MTT assays [11]. The 50% cytotoxic concentration (CC$_{50}$) was defined as the concentration of the compound which reduced the cell viability by 50%, compared to that of untreated controls. The selectivity index (SI) was defined as the CC$_{50}$ to IC$_{50}$ ratio.

Gel Electrophoresis and Quantitative Assays of Proteins.

Polyacrylamide gel electrophoresis of SDS-denatured protein samples (SDS-PAGE), and immunoblotting analysis have been described in detail in previous studies [1,2]. Briefly, proteins were electrophoresed in SDS-denaturing, 10%- or 15%-polyacrylamide gel, along with prestained protein markers (PageRuler™ prestained protein ladder; Fermentas Inc., Hanover, Md., or Dual Color™ Standards, Bio-Rad), and electrically transferred to nitrocellulose membrane (Hybond™-C-extra; GE Healthcare Bio-Sciences). Blots were blocked in 5% skimmed milk in Tris-buffered saline (TBS) containing 0.05% Tween-20 (TBS-T), rinsed in TBS-T, then successively incubated with primary rabbit or mouse anti-Gag antibodies, and relevant anti-IgG secondary antibodies, at working dilutions ranging from 1:1,000 to 1:10, 000. Anti-HIV-1 Gag polyclonal antibody (laboratory-made; [9]) was raised in rabbit by injection of bacterially-expressed, GST-fused and affinity-purified C-truncated Gag protein consisting of full-length MA domain and the first seventy-eight residues of the CA domain (Pst I site; gag$_{Lai}$ sequence).

Mouse monoclonal antibody (mAb) anti-CAp24 (Epiclone #5001) and mAb anti-MAp17 (Epiclone #5003) were obtained from Cylex Inc. (Columbia, Md.). Mouse monoclonal anti-oligo-histidine antibody was purchased from Quiagen S.A. (Courtaboeuf, France). Phosphatase-labeled anti-rabbit, or anti-mouse IgG conjugates were purchased from Sigma (St Louis, Mo.). For immunological quantification of VLP or VLP protein content, membrane-transferred protein were reacted with their specific primary antibody, then with $^{125}$I-labeled protein A (MP Biomedicals France, 67402 Illkirch; specific activity 30 µCi/µg) used at 20-30 µCi per 100 cm$^2$ membrane, and exposed to radiographic films (Kodak BioMax HE Film™, Sigma-Aldrich, 38297-St Quentin-Fallavier). Autoradiograms were scanned and quantitated by densitometric analysis, using the VersaDoc image analyzer and the Quantity One program (BioRad), or protein bands were excised from blots and radioactivity measured in a scintillation counter (Beckman LS-6500), as previously described [8,9]. Alternatively, quantification of proteins in VLP was also performed using radiolabeling of proteins. Baculovirus-infected cells samples were labeled with $^{35}$S-amino acids (ICN Pharmaceuticals France, 91898-Orsay; Tran$^{35}$S-LABEL™; specific activity >1,000 Ci/mmol), added at 15 µCi/ml in methionine-free medium for 30 h at 18 h pi in the absence or presence of inhibitor in DMSO. VLP were recovered from the cell culture medium as described above, and radioactive proteins analysed by SDS-PAGE and autoradiography of dried gels.

Electron Microscopy and Immuno-Electron Microscopy.

Baculovirus-infected Sf9 cells were harvested at 48 h pi, pelleted, fixed with 2.5% glutaraldehyde in 0.1 M phosphate buffer, pH 7.5, post-fixed with osmium tetroxide (2% in H$_2$O) and treated with 0.5% tannic acid solution in H$_2$O. The specimens were dehydrated and embedded in Epon (Epon-812; Fulham, Latham, N.Y.). Ultrathin sections were stained with 2.6% alkaline lead citrate and 0.5% uranyl acetate in 50% ethanol, and post-stained with 0.5% uranyl acetate solution in H$_2$O [8,9]. Grids were examined under a Jeol JEM-1400 electron microscope, equipped with an ORIUS™ digitalized camera (Gatan France, 78113-Grandchamp). For statistical EM analyses, a minimum of 30 grid squares containing 10 to 20 cell sections each were examined for counting VLP budding at the cell surface, or budding in intracellular vesicular compartment.

For immuno-electron microscopy, specimens were fixed with 4% paraformaldehyde in 0.1 M phosphate buffer pH 7.3 for 4 h, post-fixed with 1% glutaraldehyde in 0.1 M phosphate buffer pH 7.3 for 4 h, then rinsed overnight in 0.1 M phosphate buffer pH 7.3. After dehydration, specimens were included in LR White hydrophilic resin (Electron Microscopy Sciences, Hatfield, Pa.; EMS Catalog#14380), and ultrathin sections deposited on nickel-coated grids. Grids were incubated with anti-Gag rabbit antibody (laboratory-made; [9]) at a dilution of 1:50 in TBS for 1 h at room temperature (RT). After rinsing with TBS, the grids were post-incubated with 6-nm colloidal gold-tagged goat anti-rabbit IgG antibody (British Biocell International Ltd, Cardiff, UK; diluted to 1:50 in TBS) for 30 min at RT. After rinsing with TBS, the specimens were post-stained with 1% uranyl acetate in H$_2$0 for 1 min at RT, rinsed again with TBS, and examined under the electron microscope.

Chemical Cross-Linking of Intracellular Pr55Gag.

Aliquots of recombinant baculovirus-infected Sf9 cells (5×10$^5$ cells) untreated or treated with 16 at 10 ug/ml for 24 h at 24 h pi were centrifuged at low speed, resuspended in 200 µl of PBS containing the cross-linker bis(sulfosuccinimidyl) suberate (BS3; Pierce Biotechnology, Rockford, Ill.) at increasing molarities, ranging from 0 to 50 mM [12], and incubated in this buffer for 30 min at room temperature (RT). Cell samples were then centrifuged, resuspended and lysed in 200 µl 0.015 M NaCl, 0.5 mM phosphate buffer pH 7.3 containing BS3 at the same molarites as in the original mixtures, and further incubated for 30 min at RT. Cell lysates were mixed with 30 µl 6 times concentrated (6×) SDS-sample buffer without β-mercaptoethanol, heated to 100° C. for 1 min, and Gag proteins analyzed by SDS-PAGE and immunoblotting. Western blots (Amersham Hybond™-ECL; GE-Healthcare) were incubated with polyclonal anti-Gag rabbit serum (laboratory-made; [9]) diluted to 1:3,000 for 3 h at RT, followed by peroxidase-labeled anti-rabbit IgG (Sigma; dilution 1:10,000) for 1 h at RT. Blots were then reacted with SuperSignal® West Pico chemiluminescence substrate (Pierce Biotechnology), and luminograms were visualized using the Fusion X7 imaging system with the Bio 1D software (Vuilbert-Lourmat, Marne-la-Vallee, France).

Results

The compounds according to the invention were evaluated for their capacity to inhibit HIV-1 assembly and/or maturation and regarding the consequences on viral infectivity.

Capacity to Infect MAGIC-5B Cells.

To this end, viruses produced by transfection of HIV-1 NL4.3 molecular clones in 293T cells maintained in the presence of newly synthesized compounds 12, 13, 15 and 16 were analyzed for their capacity to infect MAGIC-5B cells in parallel with BA (1) and DSB (2). The bioassay data obtained are summarized in Table 1.

TABLE 1

Efficiency of inhibition of HIV-1 infection of betulinic acid derivatives[a]

| Compound | IC$_{50}$ (µM) | CC$_{50}$ (µM) | SI[b] |
|---|---|---|---|
| BA | 5.315 | 4.52 | 0.85 |
| DSB | 0.040 | 31.0 | 775.00 |
| (12) | 0.160 | 49.5 | 309.37 |
| (15) | 0.170 | 33.0 | 199.41 |
| (16) | 0.016 | 33.9 | 2118.75 |

[a]The mean values (m) for the 50% inhibitory activity (IC50) infection were given as µM (m). The mean values (m) for cytotoxicity (CC50) were given as µM (m).
[b]The selectivity index (SI) represented the CC50/IC50 ratio.

Conversion of Uncleaved p25 (CA-SP1) to Mature p24 (CA).

To further elucidate the mechanism of action, viral samples used for infection assays were subjected to biochemical characterization (FIG. 2). Analyzing conversion of uncleaved p25 (CA-SP1) to mature p24 (CA) revealed that compounds 2, 12, 15 and 16 inhibit the CA-SP1 cleavage.

Analysis of Virus Morphology.

To determine whether defect in p25 to p24 processing induced by BA, DSB, 12, 15 and 16 affected virus morphology, analysis by EM was performed. In the absence of compounds, cells transfected with pNL4-3 produced virus particles with the classical mature morphology characterized by the presence of condensed, conical cores (FIG. 3A). In contrast, virus from cells treated with DSB, 12, 15 and 16 lacked conical cores. Instead, these virions displayed spherical, acentric cores and were further distinguished from the untreated particles by the presence of an additional electron-dense layer inside the viral membrane (FIG. 3C, 3D, 3E, 3F).

In contrast, BA has a moderate effect on virus maturation inhibition. Taken together, these results indicate that DSB, 12, 15 and 16 block effectively proper virion maturation.

The compounds according to the invention function thus as maturation inhibitor and inhibit the conversion of p25 (CA-SP1) to p24 (CA) in virion lysates leading to a defective Gag processing and to the production of morphologically abnormal and noninfectious particles.

Packaging of Vpr and Vpr-Tagged Luciferase (LucVpr) Proteins into HIV-1 VLP Produced in Insect Cells.

Vpr has been found to be coencapsidated with the HIV-1 Gag precursor (Pr55Gag) in roughly equimolar ratio to Pr55Gag, a stoichiometry which was later re-evaluated to a lower ratio of 1 copy of Vpr per 7 Gag molecules [13]. Sf9 cells were coinfected with two recombinant baculoviruses at equal multiplicity (MOI 10 each), one expressing HIV-1 Pr55Gag and the other Vpr or the fusion protein LucVpr. VLP recovered from the cell culture medium at 48 h pi were analyzed by SDS-PAGE and Western blotting using anti-Gag and anti-His tag antibodies. Both Vpr and LucVpr proteins were efficiently packaged into VLP. A luciferase enzymatic activity associated was also observed with extracellular VLP recovered from cells coexpressing Pr55Gag and LucVpr, as detailed below. This suggested that (i) the LucVpr fusion protein was competent for packaging into VLP, and (ii) that the luciferase moiety of LucVpr retained its enzymatic activity after fusion with Vpr. Since some luciferase enzyme could be carried over during VLP purification, the next set of experiments were designed to discriminate between VLP-adsorbed and VLP-incorporated material.

Specificity of LucVpr Encapsidation into VLP: Gag-p6 Domain-Dependence.

To determine whether the luciferase activity that was found associated with HIV-1 VLP represented encapsidated LucVpr, and not enzyme contaminants adsorbed onto VLP, we coinfected SD cells with AcMNPV-LucVpr and AcMNPV-GagΔp6, a recombinant baculovirus which expressed a p6-deleted version of HIV-1 Gag precursor. In previous studies, we have shown that the p6 domain is dispensable for VLP budding and egress from recombinant baculovirus-infected insect cells, and, interestingly, that VLP constituted of p6-deleted Gag precursor molecules (GagΔp6 of 47 kDa) showed a more regular shape and higher sphericity than VLP constituted of WT Pr55Gag [3]. SD cells coinfected with AcMNPV-LucVpr and AcMNPV-Pr55Gag (full-length, wild-type Gag precursor) served as positive control, and for negative control for VLP production, Sf9 cells were infected with AcMNPV-LucVpr alone.

Cell culture medium of SD cells coexpressing LucVpr and Pr55Gag or GagΔp6 was collected at 48 h pi, using ultracentrifugation through a sucrose cushion followed by a second step of ultracentrifugation in isopycnic gradient [8,9]. The gradient fractions were analyzed for Gag polyprotein content (FIG. 4a) and processed for luciferase assay (FIG. 4b). Samples from cells coexpressing Pr55Gag+LucVpr showed a peak of luciferase activity which coincided with the apparent density of VLP in sucrose-$D_2O$ density, viz. 1.15-1.25 [8,9]. In contrast to these control samples, no significant luciferase activity was detected in the VLP-containing fractions from the culture medium of GagΔp6+LucVpr-coexpressing cells: the level of luciferase activity observed was comparable to the background level found in culture medium of cells infected with AcMNPV-LucVpr alone (FIG. 4b). This result suggested that the luciferase activity that we found associated with membrane-enveloped HIV-1 VLP was packaging-specific, and resulted from a p6-dependent packaging process mediated by the Vpr moiety of the LucVpr fusion protein.

Quantification of VLP Assembly Based on Luciferase Assay, as Applied to the Prototype Assembly Inhibitor PA-457.

Sf9 cells were coinfected with AcMNPV-Pr55Gag and AcMNPV-LucVpr (at a MOI of 10 each), and DSB added to the cell culture at 24 h pi at increasing doses, ranging from 0 to 10 µg/ml, and maintained for 24 h. Cell culture medium was then harvested at 48 h pi, subjected to the 2-step ultracentrifugation analysis, and each gradient fraction probed for Gag polyprotein and luciferase activity, as above. We observed that the peak of VLP-associated luciferase activity progressively decreased in a DSB dose-dependent manner (FIG. 5). The gradient fractions corresponding to the peak of luciferase activity were pooled, and the VLP contained in these fractions were pelleted, lysed and assayed for luciferase content. The luciferase activity was determined in parallel in the corresponding cell lysates, and the values of the ratio of VLP-associated to intracellular luciferase activity were plotted versus the DSB concentrations. The curve confirmed the dose-dependent decrease of VLP-associated luciferase in the presence of DSB. It correlated with the progressive diminution of the levels of extracellular VLP, as shown by the Pr55Gag signal in Western blot analysis. The intracellular expression of Pr55Gag remained virtually unchanged within this range of DSB concentrations, as already observed [8].

These data suggested that a luciferase assay based on the VLP-packaging of LucVpr fusion protein could legitimately be used to quantitate the VLP production and evaluate the efficacy of antivirals acting at the stage of virus particle assembly and extracellular budding. As exemplified by this particular experiment, the 50% inhibition VLP formation was observed at a DSB concentration of 2.2-2.5 µg/ml, corresponding to an $IC_{50}$ of 3.8-4.2 µM. This value was consistent with the $IC_{50}$ value of 8-10 µM previously determined using an immuno-radiochemical assay of VLP [8], a method which could not compare with the luciferase assay, in terms of sensitivity and linearity of the response over a wide range of enzyme concentrations.

However, the possibility that DSB (or any member of this class of inhibitors) might negatively interfere with cellular functions indirectly involved in the copackaging of LucVpr and Pr55Gag was envisaged. To address this issue, we labeled baculovirus infected cell cultures with $^{35}S$-methionine and $^{35}S$-cysteine, purified the $^{35}S$-labeled VLP by ultracentrifugation, and analyzed their protein content using SDS-PAGE, and autoradiography and Western blotting. Gag and Vpr protein bands were excised from the gel and their respective radioactivity content determined by scintillation counting. Of note, Gag was evaluated as the whole Gag content, including all Gag protein species in our calculation, i.e. Pr55Gag, Pr41Gag, CAp24, and MAp17, and corrected for the respective content of sulfur-containing amino acid residues in the different protein species. We found an average molecular ratio of 5.60±0.68 copies of Gag per Vpr molecule (m±SD; n=8) in VLP produced by Sf9 cells, a value which was close to the value of 7:1 reported for HIV-1 virions released by human cells [13].

The same protocol was applied to VLP isolated from PA-457-treated Sf9 cells coexpressing LucVpr and Pr55Gag. When plotted versus the DSB doses, the Gag-to-LucVpr ratios remained virtually constant, regardless of the DSB dose, with an average value of 4.92±0.25 copies of Gag per LucVpr molecule (m±SD; n=8). The absence of significant decrease of the LucVpr:Gag ratio in the presence of increasing doses of DSB therefore excluded a possible direct interference of DSB with the LucVpr encapsidation machinery, which could result in apparent lower values of luciferase activity at high DSB concentrations.

The minor difference in the mean values of Vpr:Gag and LucVpr:Gag ratios (5.60±0.68 versus 4.92±0.25) was not significant at the P=0.05 level, and suggested that the fusion of luciferase to the N-terminus of Vpr did not significantly alter the encapsidation efficiency of the LucVpr fusion protein, compared to nonfused Vpr. If one considered an average value of 1 copy of Vpr or LucVpr per 5 Gag molecules (ca. 20%) the packaging of Vpr and LucVpr into VLP produced in Sf9 cells was as efficient as the packaging of Vpr into HIV-1 virions (15 Vpr; [13]). This important point validated our method of VLP quantification using Vpr-based luciferase assay and recombinant HIV-1 Gag precursor in the baculovirus-insect cell expression system.

Evaluation of Potential HIV-1 Assembly Inhibitors Using LucVpr Packaging-Based Assay.

BA, PA-457, 12, 15 and 16 were administered to Sf9 cells coinfected with AcMNPV-Pr55Gag and AcMNPV-LucVpr at 24 h pi, and at increasing concentrations. Drug treatment was maintained for a further 24 h, and VLP released in the cell culture medium were pelleted through a sucrose cushion [8]. The amounts of extracellular VLP recovered in the 48 h-pellets obtained in the presence of the different inhibitors were determined using the luciferase assays. After normalization to the luciferase activity determined in the corresponding cell lysates, the values of the ratio of VLP-incorporated to cell-associated luciferase activity were plotted versus the drug concentrations.

12 and 15, as well as the leader compound PA-457, showed a net inhibitory effect on VLP assembly with some differences in their respective efficacy. 15 presented the highest inhibitory activity, with $IC_{50}$ ranging between 1 and 2 µg/ml, with a mean value at 1.9 µM, versus 5.1 µM for DSB and 5.9 µM for ST-327 (FIG. 6 and Table 2 below). The selectivity index (SI) values were in the same order of magnitude for 15 and PA-457, but 3-fold lower than DSB for 12 (Table 2).

TABLE 2

Efficiency of inhibition of HIV-1 VLP assembly by betulinic acid derivatives[a].

| Compound | $IC_{50}$ (µg/ml) | $IC_{50}$ (µM) | $CC_{50}$ (µM) | SI[b] |
|---|---|---|---|---|
| BA | 18.0 ± 3.0 | 39.4 | 43.8 | 1.1 |
| DSB | 3.0 ± 1.0 | 5.1 | 93.5 | 18.7 |
| 12 | 3.8 ± 1.6 | 5.9 | 31.1 | 5.3 |
| 15 | 1.6 ± 0.5 | 1.9 | 24.7 | 13.0 |
| 16 | NA[c] | NA[c] | 120.0 | ND[d] |

[a]The mean values (m) for the 50% inhibitory activity ($IC_{50}$) on VLP assembly were given as µg/ml (mean, m ± SEM; n = 4), or as µM (m). The mean values for cytotoxicity ($CC_{50}$) were only given as µM.
[b]The selectivity index (SI) was given by the ratio $CC_{50}$:$IC_{50}$.
[c]NA, not applicable.
[d]ND, not determined.

Intriguingly, the dose-response curve of VLP assembly inhibition obtained with 16 showed a gentle slope until 8 µg/ml, followed by a plateau at 60-50% VLP production at concentrations higher than 10 µg/ml (corresponding to a molarity of 15.6 µM; FIG. 6 and Table 2). In addition, EP-39 showed the lowest level of cytotoxicity, compared to the other drugs including BA (Table 2). The plateau observed in the inhibition curve of 16 implied the occurrence of a residual production of luciferase-positive VLP in the presence of high doses of 16. This result was somehow unexpected, since 16 inhibited the maturation cleavage of CAp24-SP1 and decreased the virus infectivity with a mean $IC_{50}$ of 16 nM and a SI over 2,000 [14], i.e. a significantly higher efficiency compared to that of the leader compound PA-457. Further analysis of the 16 biological effects was then performed to exclude possible false negative results.

Biophysical Properties of Luciferase-Positive Particles Produced by 16-Treated Cells.

The extracellular VLP recovered in the 48 h-pellet of culture medium of 16-treated cells were analyzed by isopycnic ultracentrifugation in sucrose-$D_2O$ density gradient [8,9], as in the experiments of FIGS. 4 and 5. Control VLP released by untreated cells equilibrated at an apparent density of 1.15, consistent with that of membrane-enveloped retroviral particles [15]. However, residual VLP produced in the presence of 16 showed a broader peak of luciferase activity which corresponded to an average density of 1.17. This suggested heterogeneity and a change in the composition of the 16 VLP compared to control VLP, with a difference in the ratio of protein to lipids consisting of a higher proportion of proteins versus lipids in 16 VLP. Our next experiments were aimed at elucidating this point using another approach, based on a structural analysis.

Structural Analysis of 16-Particles.

In a previous study, we have shown that DSB added to cell cultures in the micromolar range had a drastic effect on virus assembly. At 10 µg/ml (17 µM), DSB totally abolished VLP budding and egress from AcMNPV-Gag-infected Sf9 cells [8]. It also completely blocked the cytoplasmic assembly of core-like particles formed of non-N-myristoylated Gag precursor [8]. By contrast, control, untreated AcMNPV-Gag-infected Sf9 cells were decorated with VLP budding in abundance from the plasma membrane [8,9]. To further investigate the molecular and cellular basis for the difference in the inhibitory effect between the three inhibitors PA-457, 12 and 15 on one hand, and 16 on the other hand, we examined by electron microscopy (EM) AcMNPV-Gag-infected Sf9 cells treated with the different drugs at 5 and 10 µg/ml for 24 h at 24 h pi. The electron microscopy (EM) pattern shown by 12- and 15-treated cells was similar to that of cells treated with DSB at the same concentrations: a net inhibitory effect on VLP assembly and budding was observed with 12 and 15.

However, Pr55Gag-expressing SD cells showed a different response to 16, with different types of EM patterns which often coexisted in the same cells. (i) Electron-dense particles of ca. 100 nm in diameter were observed within the cytoplasm, dispersed or arranged as small clusters surrounded by a membrane; (ii) 100-nm particles also accumulated in large cytoplasmic inclusions; (iii) irregular aggregates of nanoparticles of ca. 20 nm in diameter were also seen in the cytoplasm, and these nanoparticles were immunogold-labeled with anti-Gag antibody. (iv) Occasionally, 100 nm-particles were seen in the process of egressing into the extracellular milieu, directly or indirectly via vesicles opening to the milieu.

The 100-nm particles assembled in 16-treated cells differed structurally from the nonenveloped, intracytoplasmic core-like particles of 100-130 nm in diameter assembled by non-N-myristoylated Pr55Gag [8,9], and from the extracellular, membrane-enveloped VLP released by N-myristoylated Pr55Gag-expressing cells. At high magnification, sub-structures were discernible, conferring to 16-induced particles the aspect of morulae. Morula-like particles had a diameter ranging from 87 to 120 nm (mean diameter, m±SD=109.1±9.2, SD, n=14). Each morula appeared to be constituted of bead-shaped subunits resembling the nanoparticles already seen in irregular aggregates, ranging from 14 to 27 nm in diameter (m±SD=19.4±3.2; n=17). Many morula-like particles were found to be irregular in shape, and/or in the process of dismantling and releasing isolated nanoparticles.
Effect of 16 on the SP1 Domain Mutant GagA364V.

HIV-1 GagA364V is the prototype of a series of PA-457-resistant Gag mutants showing a normal or subnormal pattern of PR-mediated Gag processing in the presence of inhibitory doses of DSB [4]. Based on the resistance to DSB conferred by A364V and other mutants of similar phenotype, the alanine residue at position 364 in the Pr55Gag sequence (position 1 of the SP1 domain) and its flanking regions in the CA and SP1 domains have been assumed to represent the main target of DSB [4]. We therefore substituted the alanine residue for valine at codon-364 in the gag sequence of the baculoviral clone AcMNPV-Pr55Gag, in order to analyze the sensitivity of the GagA364V mutant to 16 in terms of assembly and budding of VLP from GagA364V-expressing cells.

Unexpectedly however, we found that the GagA364V mutant was unstable: SDS-PAGE and Western blot analyses of lysates of GagA364V-expressing cells showed that the Gag antibody-reacting proteins consisted of a barely visible band at 55 kDa, the molecular mass of uncleaved WT Pr55Gag, and a major band at 41 kDa. The Pr41Gag species corresponded to the MA-CA domains since it reacted with both anti-MA and anti-CA monoclonal antibodies. The deletion of the NC and p6 domains in Pr41Gag is known to be detrimental to VLP assembly [1]. EM analysis of GagA364V-expressing cells confirmed the Gag protein pattern: we observed very rare VLP in the process of assembly and budding at the plasma membrane or in cytoplasmic vesicles. The GagA364V mutant was verified by DNA sequencing, which showed the absence of accidental stop codon at the C-terminal end of the CA domain which would explain the occurrence of the Pr41Gag species. The data implied that a premature cleavage occurred at or near the CA-SP1 junction of the GagA364V mutant polyprotein. Host cell proteases were responsible for this cleavage since HIV-1 PR was absent from our expression system. The GagA364V unstability did not allow us to study the possible influence of the Ala-to-Val mutation at position 1 of the SP1 domain on the 16-mediated inhibition of VLP assembly.

Chemical Cross-Linking of Pr55Gag in 16-Treated and Untreated Cells.

To further analyse the mechanism of the effect of 16 on Gag polyprotein assembly, untreated and 16-treated (10 µg/ml), Pr55Gag-expressing Sf9 cells were incubated with increasing concentrations of the chemical cross-linker BS3 at 48 h pi for 30 min at room temperature, then lysed in hypotonic medium in the presence of BS3 used in the same range of concentrations. The oligomeric status of the Gag proteins was assessed by SDS-PAGE and Western blot analysis, using anti-Gag antibody, peroxidase-labeled complementary antibody and enhanced chemiluminescence (ECL). In control, non-cross-linked samples, the proportion of Pr41Gag (the major spontaneous cleavage product of Pr55Gag) was higher in 16-treated cells compared to untreated cells. This suggested that 16 modified the conformation of Pr55Gag and made it more sensitive to cellular proteases. In cross-linked samples without 16 treatment, the band of Pr55Gag monomers decreased rapidly at BS3 concentrations higher than 10 mM BS3, and in a dose-dependent manner. The decrease was less pronounced in 16-treated samples.

Differences in the pattern of Pr55Gag oligomers between untreated and 16-treated cells were also observed, as evidenced on overexposures and enlargements of the luminograms of Western blots. A discrete band of anti-Gag reacting protein migrating with an apparent molecular mass of 140-150 kDa and compatible with the status of Gag trimers, was detected at between 2 and 10 mM BS3 in control samples. This band disappeared at higher BS3 concentrations, while, in parallel, anti-Gag reacting material of high molecular mass became visible as a smear within the spacer gel or the loading wells. In 16-treated samples however, the band of putative Gag trimers progressively was maximum at 25 mM BS3, and still detectable up to 50 mM. This suggested that 16 favored the occurrence and/or the stability and persistence of Gag trimers, versus higher order oligomers, as compared to control samples. The cross-linking pattern of Gag in situ confirmed our EM observation, and indicated that the Gag oligomerization status and the mode of particle assembly were different in untreated and 16-treated cells.

III. Determination of Interactions of Compound 16 with Wild Type CA-SP1-NC

2D NMR NOESY (Nuclear Overhauser Effect SpectroscopY) demonstrating the interaction between the CA-SP1—NC junction and compound 16 was recorded at 293K on a 600 Mhz Bruker Avance spectrometer equipped with a 5 mm triple resonance inverse probe and a XYZ gradient unit. Two spectra (2D 1H-1H NOESY) were recorded for the peptide CA-SP1-NC (250 µM) in absence and in presence of compound 16 (550 µM) and superimposed, at a pH of 3.8, in H2O/TFE (70/30) mixture to prevent aggregation, DMSO-d6 (1%) and a spectral width of 5296.6 Hz in both dimensions. Water suppression was achieved by using excitation sculpting with a 2 ms selective Gaussian pulse at the water signal frequency and a 250 ms mixing time. The amino acid sequence of the wild type CA-SP1-NC domain used in the study is shown in FIG. 1A. The wild type CA-SP1-NC domain contains 48 amino acids (N. Morellet, S. Druillennec, C. Lenoir, S. Bouaziz, B. P. Rogues, Helical structure determined by NMR of the HIV-1 (345-392)Gag sequence, surrounding p2: implications for particle assembly and RNA packaging, Protein. Sci., 14 (2005) 375-386.).

2D 1H-1H NOESY spectra showing the superimposition of the HN-Hα regions of the wild type CA-SP1-NC peptide in absence and in presence of compound 16 is shown in FIG. 1B. The perturbation of the chemical shifts of the peptide by addition of compound 16 are boxed and numbered on the spectra. The chemical shift perturbation has been reported on a histogram and shows that the perturbation of the chemical shifts is important for residues A366, M367, V370, N372 and I376 in the SP1 region (FIG. 1C).

REFERENCES

1. Carrière C, Gay B, Chazal N, Morin N, Boulanger P (1995) Sequence requirement for encapsidation of deletion mutants and chimeras of human immunodeficiency virus type 1 Gag precursor into retrovirus-like particles. J Virol 69: 2366-2377.
2. Chazal N, Carrière C, Gay B, Boulanger P (1994) Phenotypic characterization of insertion mutants of the human immunodeficiency virus type 1 Gag precursor expressed in recombinant baculovirus-infected cells. J Virol 68: 111-122.
3. Gay B, Tournier J, Chazal N, Carrière C, Boulanger P (1998) Morphopoietic determinants of HIV-1 GAG particles assembled in baculovirus-infected cells. Virology 247: 160-169.
4. Aiken C, Chen C H (2005) Betulinic acid derivatives as HIV-1 antivirals. Trends Mol Med 11: 31-36.
5. Yao X J, Rougeau N, Duisit G, Lemay J, Cohen E A (2004) Analysis of HIV-1 Vpr determinants responsible for cell growth arrest in *Saccharomyces cerevisiae*. Retrovirology 1: 21.

6. Selig L, Pages J-C, Tanchou V, Prévéral S, Berlioz-Torrent C, et al. (1999) Interaction with the p6 domain of the Gag precursor mediates incorporation into virions of Vpr and Vpx proteins from primate lentiviruses. J Virol 73: 592-600.
7. Muriaux D, Mirro J, Harvin D, Rein A (2001) RNA is a structural element in retrovirus particles. Proc Natl Acad Sci USA 98: 5246-5251.
8. DaFonseca S, Blommaert A, Coric P, Hong S S, Bouaziz S, et al. (2007) The 3-O-(3',3'-dimethylsuccinyl) derivative of betulinic acid (DSB) inhibits the assembly of virus-like particles in HIV-1 Gag precursor-expressing cells. Antiviral Ther 12: 1185-1203.
9. Huvent I, Hong S S, Tournier C, Gay B, Tournier J, et al. (1998) Interaction and co-encapsidation of HIV-1 Vif and Gag recombinant proteins. J Gen Virol 79: 1069-1081.
10. Hong S S, Karayan L, Tournier J, Curiel D T, Boulanger P A (1997) Adenovirus type 5 fiber knob binds to MHC class 1 alpha2 domain at the surface of human epithelial and B lymphoblastoid cells. EMBO J. 16: 2294-2306.
11. Mosmann T (1983) Rapid colorimetric assay for cellular growth and survival: Application to proliferation and cytotoxicity assays. J Immunol Methods 65: 55-63.
12. Knoller S, Shpungin S, Pick E (1991) The membrane-associated component of the amphiphile-activated, cytosol-dependent superoxide-forming NADPH oxidase of macrophages is identical to cytochrome b559. J Biol Chem 266: 2795-2804.
13. Müllner B, Tessmer U, Schubert U, Kräusslich H-G (2000) Human immunodeficiency virus type 1 Vpr protein is incorporated into the virion in significantly smaller amounts than Gag and is phosphorylated in infected cells. J Virol 74: 9727-9731.
14. Turcaud S, Chazal N, Conic P, Souquet F, Briand L, et al. (2011) Synthesis of new derivatives of Bevirimat, showing a higher activity against HIV-1 maturation. J Med Chem, submitted.
15. Wilk T, Gross I, Gowen B E, Rutten T, de Haas F, et al. (2001) Organization of immature human immunodeficiency virus type 1. J Virol 75: 759-771.

The invention claimed is:

1. A compound of the following formula (I):

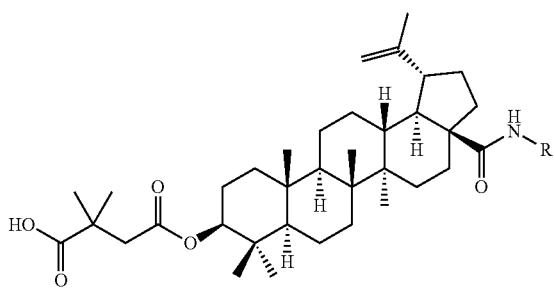

(I)

or a pharmaceutically acceptable salt thereof, a stereoisomer or a mixture of stereoisomers in any proportion, in which R represents a $(C_1$-$C_{10})$alkyl group substituted with one or more $NHR^1$, with $R^1$ representing a hydrogen atom or a -Alk, —C(O)-Alk or —C(O)O-Alk group, Alk representing a $(C_1$-$C_6)$ alkyl group.

2. The compound according to claim 1, characterized in that R represents a $(C_1$-$C_6)$alkyl group substituted with one or more $NHR^1$.

3. The compound according to claim 1, characterized in that R represents a group —$(CHR^2)$—$(CHR^3)_n$—X, in which:

n represents 0 or 1,

X represent a group COOH or $NHR^1$, and $R^2$ and $R^3$ represent, independently of each other, a hydrogen atom or a $(C_1$-$C_8)$alkyl group, substituted with $NHR^1$.

4. The compound according to claim 1, characterized in that $R^1$ represent a hydrogen atom or a —C(O)O-Alk group.

5. The compound according to claim 1, characterized in that R is chosen from the following groups:

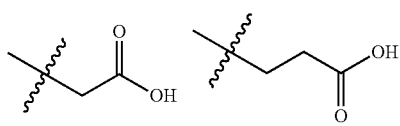

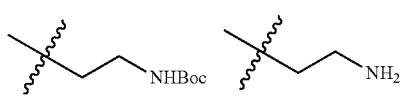

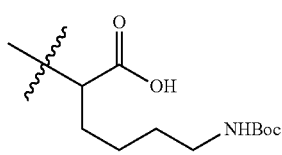

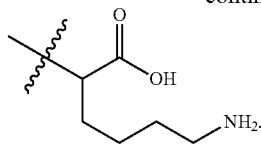

6. A compound according to claim 1 in a dose amount between 0.01 mg and 1000 mg.

7. A method for treating an infection with a retrovirus comprising administering to a person in need of such treatment a compound according to claim 1.

8. A pharmaceutical composition comprising at least one compound according to claim 1 and at least one pharmaceutically acceptable vehicle.

9. A method for preparing a compound according to claim 1, comprising the following successive steps:

(i) reaction of a compound of the following formula (II):

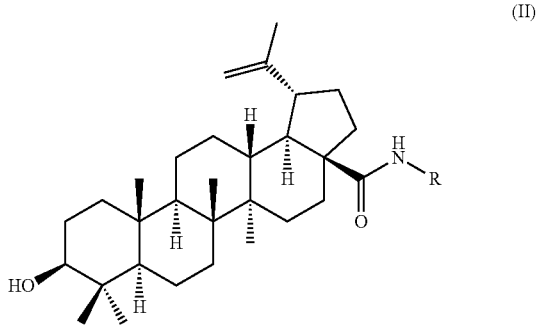

(II)

in which R represents a $(C_1$-$C_{10})$alkyl group substituted with one or more $NHR^1$, with $R^1$ representing a -Alk, —C(O)-Alk or —C(O)O-Alk group, Alk representing a $(C_1$-$C_6)$alkyl group, with 2,2-dimethylsuccinic anhydride, and (ii) optionally, when R comprises a $NHR^1$ group, deprotection of this $NHR^1$ group to yield a $NH_2$ group.

10. The method according to claim 9, characterized in that the compound of formula (II) is prepared according to the following successive steps:

(a) coupling between a compound of formula (III)

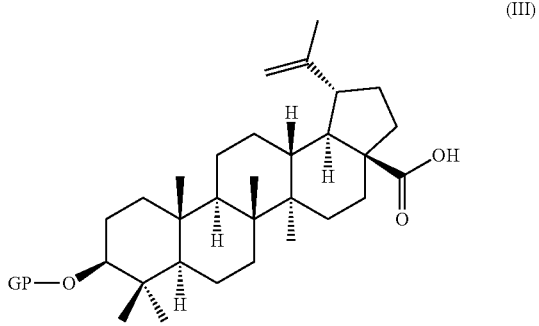

(III)

in which GP represents a O-protecting group, with an amine of the following (IV):

in which $R^4$ represents a $(C_1-C_{10})$alkyl group substituted with one or more groups chosen from COO-Alk$^1$ and NHR$^1$, with R$^1$ representing a -Alk, —C(O)-Alk or —C(O)-Alk group, Alk and Alk$^1$ representing, independently from one another, a $(C_1-C_6)$alkyl group, to yield a compound of the following formula (IV):

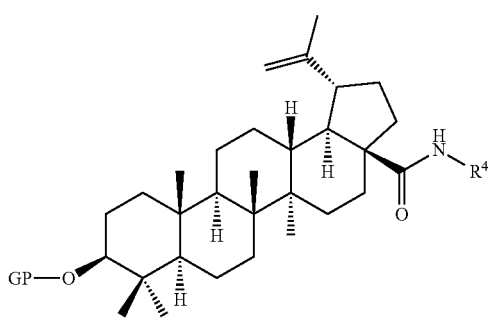

in which $R^4$ and GP are as defined above, and (b) deprotection of the hydroxyl group and, when appropriate, the —COO-Alk$^1$ group of the compound of formula (IV) obtained in the previous step (a) to yield a compound of formula (II).

11. The compound of claim 1 wherein the mixture of stereoisomers is a mixture of enantiomers.

12. The compound if claim 1 wherein the mixture of stereoisomers is a racemate mixture.

13. The compound of claim 1 wherein R represents a $(C_1-C_{10})$alkyl group substituted with one or two groups being NHR$^1$.

14. The compound according to claim 1, characterized in that R represents a $(C_1-C_6)$alkyl group substituted with one or two groups being NHR$^1$.

15. The compound according to claim 1, characterized in that R represents a group —(CHR$^2$)—(CHR$^3$)$_n$—X, in which:

n represents 0 or 1,

X represent a group COOH or NHR$^1$, and $R^2$ and $R^3$ represent, independently of each other, a hydrogen atom or a $(C_1-C_4)$alkyl group, substituted with NHR$^1$.

16. The compound according to claim 1, characterized in that R represents a group —(CHR$^2$)—(CHR$^3$)$_n$—X, in which:

n represents 0 or 1,

X represent a group COOH or NHR', and $R^2$ and $R^3$ represent, independently of each other, a hydrogen atom or a $(C_1-C_8)$alkyl group substituted with NHR$^1$, and wherein at least $R^2$ or $R^3$ represents a hydrogen atom.

17. The compound according to any of claim 1, characterized in that R$^1$ represents a hydrogen atom or a tert-butyloxycarbonyl group.

18. A method for treating an infection with HIV comprising administering to a person in need of such treatment a compound according to claim 1.

19. A method for treating an infection with HIV-1 comprising administering to a person in need of such treatment a compound according to claim 1.

20. A method for preparing a compound according to claim 1 comprising the following successive steps:

(i) reaction of a compound of the following formula (II):

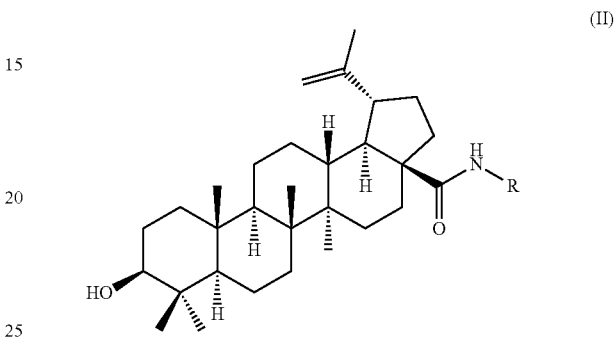

in which R represents a $(C_1-C_{10})$alkyl group substituted with one or two NHR$^1$, with R$^1$ representing a -Alk, —C(O)-Alk or —C(O)O-Alk group, Alk representing a $(C_1-C_6)$alkyl group, with 2,2-dimethylsuccinic anhydride, and (ii) optionally, when R comprises a NHR$^1$ group, deprotection of this NHR$^1$ group to yield a NH$_2$ group.

21. The method according to claim 9, characterized in that the compound of formula (II) is prepared according to the following successive steps:

(a) coupling between a compound of formula (III)

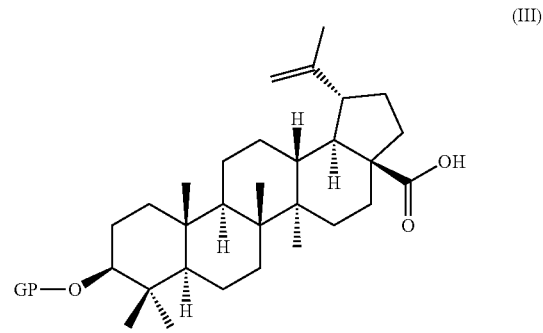

in which GP represents an acetyl group, with an amine of the following (IV):

in which R$^4$ represents a $(C_1-C_{10})$alkyl group substituted with one or two groups chosen from COO-Alk$^1$ and NHR$^1$, with $R^1$ representing a -Alk, —C(O)-Alk or —C(O)O-Alk group, Alk and $Alk^1$ representing, independently from one another, a $(C_1-C_6)$alkyl group, to yield a compound of the following formula (IV):

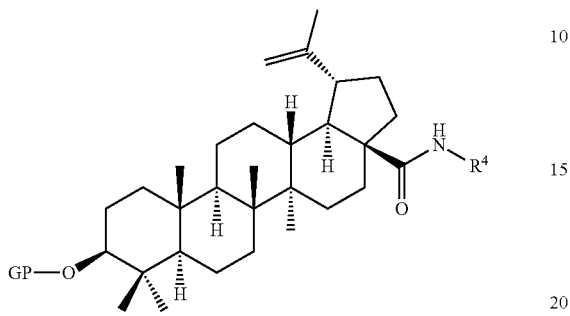

(IV)

in which $R^4$ and GP are as defined above, and (b) deprotection of the hydroxyl group and, when appropriate, the —COO-$Alk^1$ group of the compound of formula (IV) obtained in the previous step (a) to yield a compound of formula (II).

\* \* \* \* \*

UNITED STATES PATENT AND TRADEMARK OFFICE
CERTIFICATE OF CORRECTION

PATENT NO. : 9,056,888 B2
APPLICATION NO. : 13/608486
DATED : June 16, 2015
INVENTOR(S) : Bouaziz et al.

Page 1 of 1

It is certified that error appears in the above-identified patent and that said Letters Patent is hereby corrected as shown below:

On the title page item [73]

delete

"Centre National de la Recherche Scientifique (FR)"

insert

--Centre National de La Recherche Scientifique (FR)--

Signed and Sealed this
Third Day of May, 2016

Michelle K. Lee
*Director of the United States Patent and Trademark Office*

UNITED STATES PATENT AND TRADEMARK OFFICE
CERTIFICATE OF CORRECTION

PATENT NO.       : 9,056,888 B2
APPLICATION NO.  : 13/608486
DATED            : June 16, 2015
INVENTOR(S)      : Bouaziz et al.

It is certified that error appears in the above-identified patent and that said Letters Patent is hereby corrected as shown below:

In the claims

Column 33, Claim 1, Line 6:
delete "$NHR^1$" and insert -- -$NHR^1$ --

Column 35, Claim 16, Line 59:
delete "NHR'" and insert -- $NHR^1$ --

Signed and Sealed this
Fourteenth Day of June, 2016

Michelle K. Lee
*Director of the United States Patent and Trademark Office*